(12) United States Patent
Fischell et al.

(10) Patent No.: US 6,473,639 B1
(45) Date of Patent: Oct. 29, 2002

(54) NEUROLOGICAL EVENT DETECTION PROCEDURE USING PROCESSED DISPLAY CHANNEL BASED ALGORITHMS AND DEVICES INCORPORATING THESE PROCEDURES

(75) Inventors: David R. Fischell, Fair Haven; Jonathan Harwood, Rumson, both of NJ (US); Benjamin D. Pless, Atherton, CA (US)

(73) Assignee: Neuropace, Inc., Sunnyvale, CA (US)

( * ) Notice: Subject to any disclaimer, the term of this patent is extended or adjusted under 35 U.S.C. 154(b) by 0 days.

(21) Appl. No.: 09/517,797

(22) Filed: Mar. 2, 2000

(51) Int. Cl.[7] ................................................. A61B 5/00
(52) U.S. Cl. ...................................................... 600/544
(58) Field of Search .............................. 600/544, 545, 600/306

(56) References Cited

U.S. PATENT DOCUMENTS

| | | |
|---|---|---|
| 3,531,561 A | 9/1970 | Trehu |
| 3,565,066 A | 2/1971 | Roaf et al. |
| 3,636,956 A | 1/1972 | Schneider |
| 3,960,151 A | 6/1976 | Kuhn |
| 3,993,046 A | 11/1976 | Fernandez et al. |
| 4,429,690 A | 2/1984 | Angelino-Pievani |
| 4,523,591 A | 6/1985 | Kaplan et al. |
| 4,566,464 A | 1/1986 | Piccone et al. |
| 4,702,254 A | 10/1987 | Zabara |
| 4,781,183 A | 11/1988 | Casey et al. |
| 4,867,164 A | 9/1989 | Zabara |
| 4,878,498 A * | 11/1989 | Abrams et al. ............. 600/544 |
| 4,905,680 A | 3/1990 | Tunc |
| 4,979,511 A | 12/1990 | Terry, Jr. |
| 5,025,807 A | 6/1991 | Zabara |
| 5,031,618 A | 7/1991 | Mullett |
| 5,129,903 A | 7/1992 | Luhr et al. |

(List continued on next page.)

FOREIGN PATENT DOCUMENTS

| | | |
|---|---|---|
| DE | 8528003 | 2/1986 |
| DE | 8706912 | 10/1987 |
| DE | 3701765 C1 | 6/1988 |
| DE | 4028021 C1 | 5/1991 |
| EP | 0 195 455 A1 | 9/1986 |
| EP | 0 195 455 B1 | 9/1986 |
| EP | 0 276 153 A3 | 7/1988 |
| EP | 0 276 153 A2 | 7/1988 |
| EP | 0 290 138 A3 | 11/1988 |
| EP | 0 290 138 A2 | 11/1988 |
| EP | 0 290 138 B1 | 11/1988 |
| EP | 0 291 632 B1 | 11/1988 |
| EP | 0 291 632 B2 | 11/1988 |
| EP | 0 291 632 A1 | 11/1988 |
| EP | 0 347 658 A1 | 12/1989 |
| EP | 0 347 658 B1 | 12/1989 |
| EP | 0 491 983 B1 | 7/1992 |
| EP | 0 491 983 A1 | 7/1992 |
| GB | 2140523 | 11/1984 |
| GB | 0 433 852 | 3/1996 |

OTHER PUBLICATIONS

Andriano, K.P. et al. (1994). "Processing and Characterization of Absorbable Polyactide Polymers for Use in Surgical Implants," *Journal of Applied Biomaterials* 5:133–140.

Chkhenkeli, S.A. and Chkhenkeli, I.S. (1997). "Effects of Therapeutic Stimulation of Nucleus Caudatus on Epileptic Electrical Activity of Brain in Patients with Intractable Epilepsy," *Stereotact Funct Neurosurg* 69:221–224.

(List continued on next page.)

*Primary Examiner*—Kevin Shaver
*Assistant Examiner*—Navin Natnithithadha
(74) *Attorney, Agent, or Firm*—Morrison & Foerster LLP

(57) ABSTRACT

This invention relates generally to information processing techniques used in the treatment of epilepsy and to devices for using these techniques.

119 Claims, 11 Drawing Sheets

U.S. PATENT DOCUMENTS

| | | |
|---|---|---|
| 5,154,172 A | 10/1992 | Terry, Jr. et al. |
| 5,179,950 A | 1/1993 | Stanislaw |
| 5,186,170 A | 2/1993 | Varrichio et al. |
| 5,188,104 A | 2/1993 | Wernicke et al. |
| 5,205,285 A | 4/1993 | Baker, Jr. |
| 5,215,086 A | 6/1993 | Terry, Jr. et al. |
| 5,215,089 A | 6/1993 | Baker, Jr. |
| 5,222,494 A | 6/1993 | Baker, Jr. |
| 5,231,988 A | 8/1993 | Wernicke et al. |
| 5,235,980 A | 8/1993 | Varrichio et al. |
| 5,237,991 A | 8/1993 | Baker, Jr. et al. |
| 5,251,634 A | 10/1993 | Weinberg |
| 5,263,480 A | 11/1993 | Wernicke et al. |
| 5,269,303 A | 12/1993 | Wernicke et al. |
| 5,293,879 A | 3/1994 | Vonk et al. |
| 5,299,569 A | 4/1994 | Wernicke et al. |
| 5,304,206 A | 4/1994 | Baker, Jr. et al. |
| 5,311,876 A | 5/1994 | Olsen et al. |
| 5,330,515 A | 7/1994 | Rutecki et al. |
| 5,335,657 A | 8/1994 | Terry, Jr. et al. |
| 5,349,962 A | 9/1994 | Lockard et al. |
| 5,351,394 A | 10/1994 | Weinberg |
| 5,372,598 A | 12/1994 | Luhr et al. |
| 5,413,577 A | 5/1995 | Pollock |
| 5,474,547 A | 12/1995 | Aebischer et al. |
| 5,522,863 A | 6/1996 | Spano et al. |
| 5,531,778 A | 7/1996 | Maschino et al. |
| 5,540,730 A | 7/1996 | Terry, Jr. et al. |
| 5,540,734 A | 7/1996 | Zabara |
| 5,569,250 A | 10/1996 | Sarver et al. |
| 5,571,150 A | 11/1996 | Wernicke et al. |
| 5,604,204 A | 2/1997 | Ammann et al. |
| 5,676,655 A | 10/1997 | Howard, III et al. |
| 5,683,422 A | 11/1997 | Rise |
| 5,707,396 A | 1/1998 | Benabid |
| 5,707,400 A | 1/1998 | Terry, Jr. et al. |
| 5,711,316 A | 1/1998 | Elsberry et al. |
| 5,713,923 A | 2/1998 | Ward et al. |
| 5,716,377 A | 2/1998 | Rise et al. |
| 5,735,814 A | 4/1998 | Elsberry et al. |
| 5,743,860 A * | 4/1998 | Hively et al. ............... 600/544 |
| 5,752,979 A | 5/1998 | Benabid |
| 5,792,186 A | 8/1998 | Rise |
| 5,800,474 A | 9/1998 | Benabid et al. |
| 5,832,932 A | 11/1998 | Elsberry et al. |
| 5,833,709 A | 11/1998 | Rise et al. |
| 5,857,978 A * | 1/1999 | Hively et al. ............... 600/544 |
| 5,868,746 A | 2/1999 | Sarver et al. |
| 5,928,272 A | 7/1999 | Adkins et al. |
| 5,938,689 A | 8/1999 | Fischell et al. |
| 5,978,702 A | 11/1999 | Ward et al. |
| 5,995,868 A * | 11/1999 | Dorfmeister et al. ....... 600/300 |
| 6,006,124 A | 12/1999 | Fischell et al. |
| 6,016,449 A | 1/2000 | Fischell et al. |
| 6,018,682 A | 1/2000 | Rise |
| 6,024,702 A | 2/2000 | Iversen |
| 6,061,593 A * | 5/2000 | Fischell et al. ............. 600/544 |
| 6,095,148 A | 8/2000 | Shastri et al. |

OTHER PUBLICATIONS

Cooper, I.S. et al. (1974). "The Effect of Chronic Stimulation of Cerebellar Cortex on Epilepsy in Man," In *The Cerebellum, Epilepsy, and Behavior.* Cooper, I.S. et al., eds., Pleman Press:New York, pp. 119–171.

Cooper, I.S. et al. (1977/78). "Safety and Efficacy of Chronic Cerebellar Stimulation," *Appl. Neurophysiol.* 40: 124–134.

Cooper, I.S. and Upton, A.R.M. (1978). "Effects of Cerebellar Stimulation on Epilepsy, the EEG and Cerebral Palsy in Man," In *Contemporary Clinical Neurophysiology (EEG Suppl. No. 34).* Cobb, W.A. et al., eds., Elsevier Scientific Publishing: Amsterdam, pp. 349–354.

Davis, R. and Emmonds, S.E. (1992). "Cerebellar Stimulation for Seizure Control: 17–Year Study," *Stereotact. Funct. Neurosurg.* 58:200–208.

Eppley, B.L. and Sadove, A.M. (1992). "Effects of Resorbable Fixation on Craniofacial Skeletal Growth: A Pilot Experimental Study," *Journal of Craniofacial Surgery* 3(4):190–196.

Gerlach, K.L. (1993). "In–vivo and Clinical Evaluations of Poly(L–lactide) Plates and Screws for Use in Maxillofacial Traumatology," *Clinical Materials* 13:21–28.

Gotman, J. (1999). "Automatic Detection of Seizures and Spikes," *Journal of Clinical Neurophysiology* 16(2):130–140.

Osario, I. et al. (1995). "A Method for Accurate Automated Real–Time Seizure Detection," *Epilepsia*, 36(supplement 4):4.

Qu, H. and Gotman, J. (1995). "A Seizure Warning System for Long–Term Epilepsy Monitoring," *Neurology* 45:2250–2254.

Sayler, K.E. et al. (1994). "A Comparative Study of the Effects of Biodegradable and Titanium Plating Systems on Cranial Growth and Structure: Experimental Study in Beagles," *Plastic and Reconstructive Surgery* 93(4):705–713.

Schiff, S. et al. (1994). "Controlling Chaos in the Brain," *Nature* 370:615–620.

Thaller, S.R. et al. (1992). "Use of Biodegradable Plates and Screws in a Rabbit Model," *Journal of Craniofacial Surgery* 2(4):168–173.

Velasco, F. et al. (1995). "Electrical Stimulation of the Centromedian Thalamic Nucleus in Control of Seizures: Long Term Studies," *Epilepsia* 36(1):63–71.

\* cited by examiner

NEUROLOGICAL EVENT DETECTION PROCEDURE USING PROCESSED DISPLAY CHANNEL BASED ALGORITHMS AND DEVICES INCORPORATING THESE PROCEDURES

FIELD OF THE INVENTION

This invention relates generally to information processing techniques used in the treatment of epilepsy and to devices for using these techniques.

BACKGROUND OF THE INVENTION

The current state-of-the-art in workstations for processing EEG signals allow for the viewing of either monopole or bipolar montages of electrode inputs. A bipolar EEG signal represents the voltage difference between two spatially separated electrodes. Existing workstations generally do not have the capability to process and display signals produced by summing two or more monopole or bipolar EEG signals. Epileptiform activity detection software, such as that by Gotman, processes individual electroencephalogram (hereinafter "EEG") channels rather than a pre-processed aggregation of selected EEG channels. In U.S. Pat. No. 6,016,449, Fischell et. al. describe an implantable system for the processing of EEG signals. Fischell et al. further describe the use of a physician's workstation for programming a separate implantable device. Physician's Workstations may also be used independently for patient diagnosis, treatment evaluation, and pre-implantation patient testing. Although an implantable device for detecting and stopping a neurological event, such as those described in the Fischell et al. patent, may be the final patient treatment, it is highly desirable first to determine the appropriate modality of treatment and to evaluate its potential for working with an external system. It is also highly desirable that the epileptiform activity algorithms created during patient testing and evaluation then be programmable into the implantable electrical stimulation therapy device itself.

In U.S. Pat. No. 5,311,876, Olsen et al. describe detection of seizures in a patient-independent manner by use of standardization techniques. Olsen et al. do not disclose patient-specific detection customization as part of a treatment based on electrical stimulation. Systems such as those described by Olsen et al. typically are used by neurologists to accelerate the analysis of patient EEGs by identifying spikes and other abnormal EEG waveforms.

SUMMARY OF THE INVENTION

This invention is a processed display channel based system for epileptiform activity detection which is applicable both to an implantable electrical stimulation therapy device (a neuropacemaker) and to a Physician's Workstation System (PWS) used for pre-implant patient testing. The PWS, often based on a Windows PC, provides a neurologist with diagnostic tools for collecting and processing EEG signals and evaluating detection algorithms including patient specific parameters for detecting and stopping neurological events such as epileptic seizures, Parkinson's tremors, and migraines. The PWS may also be used to program a neuropacemaker with the patient specific parameters for detecting and stopping neurological events identified with the PWS.

It is understood that "EEG" is used throughout the following discussions to encompass not only electroencephalogram data from scalp (surface) electrodes, but also electrocortigram data from intracranial electrodes. The phrase "brain electrodes" is used throughout the following discussions to mean any electrodes within or near the brain including scalp (surface) electrodes and intracranial electrodes. The phrase "epileptiform activity" refers to activity within the brain of a person with epilepsy which is indicative of the disease. Epileptiform activity is present during a clinical epileptic seizure but may also sometimes occur without clinical symptoms.

In J. Clin. Neurophysiol, Vol 16, No. 2, p. 131, 1999; Gotman defines behavioral and electrographic seizures:

"A behavioral seizure is defined as the behavioral manifestations of an epileptic seizure as perceived by the patient, seen by an observer, or recorded on videotape."

An electrographic seizure (or EEG seizure) is defined as "an abnormal paroxysmal EEG pattern."

For the purposes of this application, clinical seizures include behavioral seizures as defined by Gotman as well as electrographic seizures having functional or cognitive deficits that may be identified through patient testing.

The term "onset" means the point in time at which a seizure (electrographic, behavioral or clinical) begins.

For the purposes of this application, the phrase "precursor to a seizure" and term "precursor" are defined as any one or more of the following:

1. A segment of EEG or of processed EEG signal prior to the onset (start) of an electrographic seizure,
2. A segment of EEG of processed EEG signal occurring at the start of an electrographic seizure,
3. A segment of EEG or processed EEG signal prior to the onset (start) of a clinical seizure.

For the purposes of this application, the use of the term "seizure" pertains primarily to electrographic seizures, as the processed display channel (hereinafter "PDC") based neurological event detection described herein is performed on EEG or processed EEG signals.

A "template" is defined to be any one of the following:

1. A set of algorithm detection parameters which have been programmed into a PWS or neuropacemaker.
2. The set of patient specific detection system selections used for epileptiform activity detection including PDC selection, choice of detection algorithm(s) to be used on the PDC(s), and the specific set of algorithm detection parameters which have been programmed into a PWS or neuropacemaker.

Included in this invention is the simultaneous detection by two or more detection algorithms on a single PDC signal or by two or more different detection algorithms on two or more PDC's. For example, a DC shift algorithm may be used to process a first PDC, the first PDC being created by the addition of the two or three EEG channels which best show a DC shift prior to the onset of a clinical seizure. A waveform detector may simultaneously monitor a second PDC for a 10 to 14 Hz repetitive spikey waveform. The PDC may be created by subtracting one EEG channel from another and using bandpass filtering the difference between 5 and 20 Hz.

Preferably, the PDC based seizure detector uses two PDC's (or one PDC with multiple parameter sets): a first PDC being optimized to depict or detect a precursor to a patients' seizure, and a second PDC being optimized to depict or detect epileptiform activity several seconds into to seizure. Different detection algorithms, or a single algorithm with two different sets of parameters, may be programmed to detect the precursor from the first PDC and the in-seizure epileptiform activity several seconds into the seizure from the second PDC of the first PDC. This two-PDC technique has several advantages for a responsive electrical stimulation therapy device, such as:

1. If a precursor is missed, the in-seizure epileptiform activity is still detected and stimulation applied to stop the seizure.
2. If the precursor is detected and the applied stimulation is ineffective in stopping the seizure, the in-seizure epileptiform activity would be detected and a second stimulation with the same (or, perhaps, an increased) current can be applied.
3. If there is a "false positive" precursor detection where a stimulation is applied and the stimulation induces epileptiform activity, the second PDC and its in-seizure detector would detect the induced epileptiform activity and cause stimulation to be applied to stop the induced epileptiform activity.
4. In patients with very few seizures, a neuropacemaker may be implanted with only the in-seizure PDC implemented. When seizures occur and are detected, the EEG data for a period of time before the detection would be stored by the neuropacemaker. The recorded data would be used to improve the seizure detection program through identification of the seizure precursor allowing selection of first of the two PDC's. Such data recording is disclosed by Fischell in U.S. Pat. No. 6,016,449.
5. Another option for patients with very few seizures is to have epileptiform activity induced by stimulation during pre-implant testing using the PWS. During such testing, the in-seizure detector would be optimized to detect the induced epileptiform activity. The neuropacemaker would then be implanted with the stimulator enabled with the in-seizure detector programmed with the optimized parameters established during the pre-implant testing. This type of calibration is discussed by Fischell and Morel in U.S. Patent application Ser. No. 09/323,407, the entirety of which is incorporated by reference.

The PDC or PDC's may be configured to detect or exhibit features which resemble, but are not, epileptiform activity, such as "sleep spindles". If such is the case, the present invention may be used in the following ways:

1. If the false activity is found in an EEG channel or combination of EEG channels which do not exhibit the early presence of epileptiform activity, then a first PDC would be created which shows both the early onset of epileptiform activity and the false activity. A second PDC would be created which shows only the false activity. A set of logical operations shown below describe the determination or declaration of a valid detection in the event appropriate detections occur in the first PDC and not in the second PDC.
2. The specificity of detecting an individual's epileptiform activity is improved by determining whether an EEG is more like previously characterized epileptiform activity, or more like other neurological events such as sleep spindles within the same patient which may mimic the signals associated with epileptiform activity.

In one inventive variation, the EEG from each PDC is decomposed into the features used by the neurological event detection algorithms by a pre-processor. The features from each PDC may then be compared against a number of parameter sets (templates) from each algorithm wherein each parameter set is adjusted to detect different neurological events (e.g. onset of epileptiform activity, in-seizure epileptiform activity, sleep spindles, gamma waves, etc.). The software in the implanted device may then analyze an EEG segment from the PDC's and evaluate its similarity to a variety of neurological events. For example, an exemplified EEG segment may satisfy the detection requirements both for epileptiform activity and for sleep spindles if the two events have similar morphologies within an individual patient. In such an instance, it is desirable to determine which template is a closer fit for the EEG segment. Such a discrimination may be performed in a variety of mathematical ways: e.g., by weighting the importance of each parameter in the algorithm and then summing the differences between the measured EEG characteristics and the corresponding template parameters for epileptiform activity and sleep spindles. The smaller sum is used to select the appropriate corresponding template and hence the diagnosis for the EEG segment.

This example used sleep spindles as an event which might cause a false detection, but any confounding EEG that is similar in morphology to epileptiform activity is suitable for improved discrimination by this technique. In some cases, an initial template match might not discriminate between epileptiform activity and a sleep spindle (or other EEG segment similar to epileptiform activity). If analysis of the EEG segment shows that the EEG segment is essentially equally similar to both templates, the invention herein will provide the option to delay detection for a period of time (typically 300 to 1500 milliseconds). In so doing the temporal progression of the EEG activity is monitored to improve detection specificity. This additional spatio-temporal aspect of the detection algorithm takes advantage of the observation that epileptiform activity spreads to different electrodes at a different rate and with a different progression than does other neurological events in the same patient.

The present invention includes many different algorithms for processing PDC's to detect neurological events, such as Amplitude Duration, DC Shift, Waveform, Zero Crossing, Quiescent Period, and Gotman detectors. This short list of detection algorithms represents only a subset of detection algorithms suitable for use in neurological signal processing applied to PDC's. Indeed, combinations of such algorithms may be tailored to provide specific PDC results, in various orders (permutations). Thus a very large number of possible processing algorithms are possible.

DEFINITIONS

The "amplitude duration" detector compares the average Root Mean Squared (hereinafter "RMS") amplitude "A" in a PDC over a time duration "D" to a threshold "T".

The "DC shift" detector looks for a shift of the DC component of the PDC signal by a given amount of amplitude for a specified time, thus requiring two detection parameters: amplitude (V) and minimum time ($T_{min}$). An alternate embodiment of the DC shift detector uses a "not to exceed threshold" $V_n$ that would define a more limited DC range that must be between V and $V_n$ for the minimum time $T_{min}$ to indicate a neurological event.

The "waveform" detector breaks the PDC signal into half wave units. The waveform detector then counts the number of half waves of at least a minimum duration with a minimum amplitude for a specified period of time and compares this number against a preset threshold, thus requiring four detection parameters for the waveform detector algorithm. The four detection parameters are half wave minimum amplitude ($A_{min}$), half wave minimum duration ($W_{min}$), number of half waves (N) and specified period of time (P).

The "zero crossing" detector compares the number of zero crossings of the PDC signal with maximum and minimum allowed number of crossings $C_{max}$ and $C_{min}$ over the time period $P_Z$.

The "quiescent period" detector looks for a reduction in the PDC's average RMS signal level below a threshold T over a time duration D.

"Gotman" epileptiform activity detection algorithms that have been published extensively in the literature [may also be used with PDC's to improve reliability.

Desirably, this invention desirably provides a neurological event detector by creating one or more Processed Display Channels (PDC's), where each PDC is a patient-specific programmable selection or combination of EEG signal channels, and then processing at least one of the PDC's with at least one neurological event detection algorithm.

Desirably, this invention provides a neurological event detector by creating one or more Processed Display Channels (PDC's), where each PDC is a patient-specific programmable selection or combination of EEG signal channels, and then processing two or more of the PDC's with at least one neurological event detection algorithm.

This invention provides a neurological event detector by creating one or more Processed Display Channels (PDC's), where each PDC is a patient-specific programmable selection or combination of EEG signal channels, and then processing at least one of the PDC's with two or more neurological event detection algorithms.

This invention preferably implements a PDC-based seizure detector within a physician's workstation to provide diagnosis, template creation, and testing for optimizing seizure detection procedures prior to implantation of an implantable electrical stimulation therapy device.

This invention includes the implementation of a PDC-based seizure detector within an implantable device such as a neuropacemaker.

Each PDC may be produced using, e.g., low, high, or bandpass filtering.

The present invention may utilize a PDC-programmable combination of EEG signal channels by the addition and/or subtraction of two or more EEG signals with either uniform or non-uniform weighting.

Algorithms used in the present invention may include:

a.) an amplitude duration detection algorithm for neurological event detection by processing of one or more PDC's, b.) a quiescent period neurological event detection algorithm for neurological event detection which looks for a reduced amplitude over a given period followed by increased activity by processing of one or more PDC's, c.) a waveform detector algorithm for neurological event detection by processing of one or more PDC's, d.) a zero crossing detector algorithm for neurological event detection by processing of one or more PDC's, and e.) a DC shift detector algorithm for neurological event detection by processing of one or more PDC's.

PDC-based neurological event detection algorithms implemented in a physician's workstation desirably are downloadable into an implantable neuropacemaker after the physician's workstation has been used to customize the detection algorithms best to detect epileptiform activity from a specific patient.

The present invention generally uses at least two PDC's and most desirably requires that a valid seizure detection be detected in all PDC's.

In another variation, the inventive procedures and devices include at least two PDC's and require that a valid seizure detection be detected in one PDC without a simultaneous or nearly simultaneous detection in a second PDC.

The PDC's and the algorithms and parameters associated therewith may be used to detect confounding non-seizure activity, such as sleep spindles, to improve epileptiform signal identification specificity.

These and other objects and advantages of this invention will become apparent to a person of ordinary skill in this art upon careful reading of the detailed description of this invention including the drawings as presented herein.

DETAILED DESCRIPTION OF THE INVENTION

This invention relates to processes for detecting and displaying electrical neural anomalies preferably using PDC's, for stimulating neural tissue, and to devices used in practicing these procedures.

A processed display channel (PDC) is a customized combination of specific EEG channels, preferably configured best to display and to detect epileptiform activity which may be present in a particular patient. In order best to detect such activity, surgeons or other operators generally use several signal detection electrodes, located at disparate locations around the head and brain, for signal intake purposes. Although it is possible that one particular electrode on a patient brings in a signal particularly ideal for monitoring or detecting epileptiform activity, such circumstances are rare; generally, several, if not many, channels should be monitored and processed best to detect epileptiform activity. Such processing may include digital signal processing of incoming signals, the customization of such signals may utilize algorithm "parameters."

It is highly desirable to apply signal processing techniques not only in series to a given incoming signal, but also to previously or temporally combined or otherwise pre-processed signals, best to detect and to observe epileptiform activity within a given patent. At the heart of this invention is highly customizable digital signal processing for multiple incoming neurological signal channels which enables accurate epileptiform signal detection by viewing or analyzing one or more processed channels which have been particularly configured to "zero in" upon epileptiform activity within the patient, if that epileptiform activity exists.

A key advantage of PDC-based epileptiform activity detection is that one or more detection algorithms may be run on signals that have already been processed and optimized to exhibit specific neurological events such as epileptiform activity or sleep spindles or the like. Rather than observing and analyzing as many as 128 EEG channels simultaneously, an operator or device having the benefit of this invention typically will be able to meet the same goals by monitoring one or two PDC's. Use of the inventive procedures and devices simplifies the processing needed for an implantable neuropacemaker where limited power and volume reduce processing capability. With such limitations, analyzing a single PDC tailored to exhibit a patient's epileptform activity would be highly desired over analyzing multiple channels in parallel.

Figure 1:
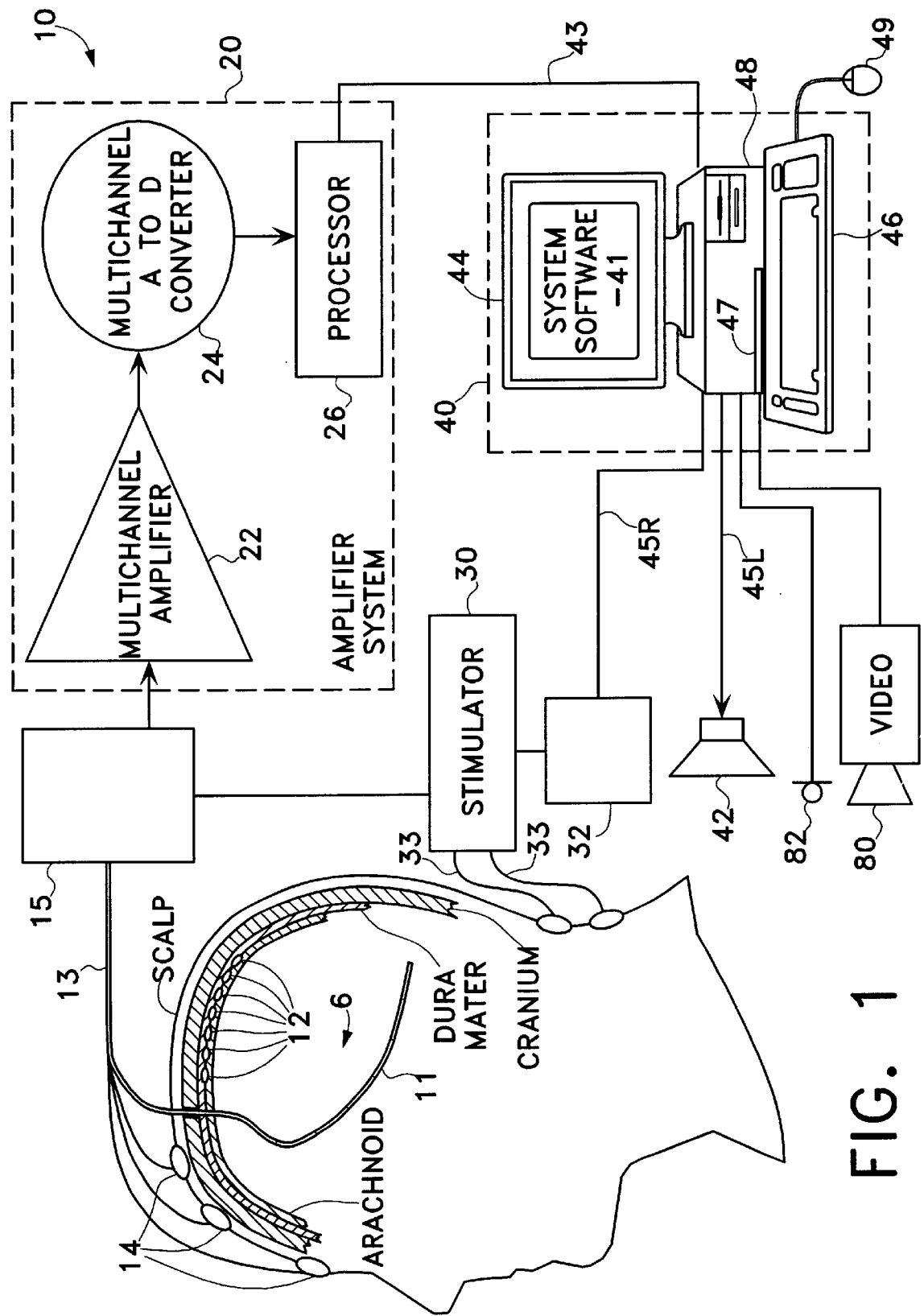
FIG. 1 is a schematic depiction of a physician's workstation system.

FIG. 1 is a schematic depiction of a physician's workstation system or device 10 controlled by a physician's workstation 40 with system software 41. A multiplicity of depth electrodes 11 is depicted, implanted deep within the patient's brain. Intracerebral depth electrodes 11, which are often line arrays of electrodes, are useful for monitoring or stimulating deep cerebral structures such as the amygdala, hippocampus, cingulate, and orbital-frontal regions which characteristically are involved in many medically refractory partial epilepsies.

In the depicted variation, a number of (or array of) brain surface electrodes 12 is placed on the surface of the patient's brain and may contain as many as 100 electrodes or more. Multiple scalp electrodes 14 are shown to be attached to the outside of the patient's head. Brain electrodes 6 comprise the depth electrodes 11, brain surface electrodes 12, scalp electrodes 14, and may also comprise electrodes placed elsewhere under the patient's scalp near or within the brain.

A multi-strand electrode cable 13 is shown connecting the scalp electrodes 14, depth electrodes 11 and brain surface electrodes 12 to an electrode interface 15. The electrode interface 15 has connectors for plugging in the electrode leads from the multi-strand cable 13. The electrode interface box connects each plugged in electrode to an amplifier system 20 comprising a multi-channel amplifier 22, multi-channel analog-to-digital (A/D) converter 24 and processor 26. The processor 26, where used, may manage settings, control, and data communications for the amplifier system 20. The patient's EEG signals coming from the electrode interface box 15 are amplified by the multi-channel amplifier 22. After amplification, the signals are digitized by A/D converter 24, and sent via a standard computer data connection (or datalink) 43 by the amplification system processor 26 to the physician's workstation 40. The depicted physician's workstation 40 has the capability to send programming over the data connection 43 to the amplifier system 20. Such programming generally comprises sampling rate, amplifier gain, high, low, notch, and bandpass filter settings, and impedance matching.

The physician's workstation 40 is typically a commercially available PC or workstation having a CPU 48, keyboard 46, mouse 49, and monitor 44. The system software 41 may run under such typical operating systems as may be found on the commercially available PC or workstation used for the physician's workstation 40.

The Synamps™ (manufactured by NeuroScan™) is an example of a typical amplifier system 20 suitable for use in this invention. The standard computer data connection 43 on the Synamps is a Small Computer System Interface (SCSI) cable. A typical CPU 48 would be an Intel Pentium II or Pentium III based PC with a Microsoft Windows NT or Windows 98 operating system with audio and video display capabilities.

When running the system software 41, the depicted physician's workstation 40 processes, stores, replays, and displays on the monitor 44, the patient's EEG signals received from the brain electrodes 6 through the amplification system 20. The depicted physician's workstation 40 also has the capability of detecting epileptiform activity and responding automatically to such detection with a stimulus. The physician's workstation 40 may connect to an electrical stimulator 30 through a triggering device 32 desirably attached, e.g., to the right audio channel output 45R of the CPU 48. Similarly a loudspeaker 42 for providing sound stimulus to the patient and/or feedback to the physician similarly may be attached to the left audio channel output 45L of the CPU 48

The electrical stimulator 30 may be connected to any electrode pair on the electrode interface box 15 allowing selective tissue stimulation via any of the depth electrodes 11 or brain surface electrodes 12. The stimulator 30 may also be attached, using wires 33, directly to skin surface electrodes 35 to provide a stimulus to the patient's skin. Such stimulation might be directed to the skin of the patient's wrist, for example.

Preferably, the system software 41 allows the operator to manually initiate patient stimulation from the physician's workstation 40. The system software 41 may also be configured to initiate patient stimulation when epileptiform activity is detected from the brain electrodes 6.

Commercial electrical stimulators such as the GRASS stimulator are suitable for use with this invention. Desirably, the stimulators are initiated by a signal from the triggering device 32 rather than by the physical act of an operator such as by a button push. Typical stimulation frequencies are between 20 and 100 Hz and typical stimulation durations are between 0.25 and 5 seconds. Bipolar pulses of duration between 0.1 and 1.0 ms with current amplitudes between 0.5 and 15 mA are typical.

The depicted physician's workstation 40 with system software 41 also provides integrated video display, data storage, and retrieval that may be synchronized with the patient EEG data. A video camera 80 may be connected to the CPU 48 as desired, e.g., through a standard parallel port, USB port, or with a video interface card 47 which is plugged into the standard data bus of the CPU 48. Video interface cards are commercially available that provide video compression, such as MPEG compression, to reduce the storage requirements for the stored video.

A microphone 82 connects into the microphone input of the CPU 48 and is used to collect audio signals along with the patient video for patient monitoring.

An Apple MacIntosh, Apple Power PC, or a Workstation running UNIX, LINUX or any other commercially available operating system may be used for the physician's workstation 40.

Figure 2:
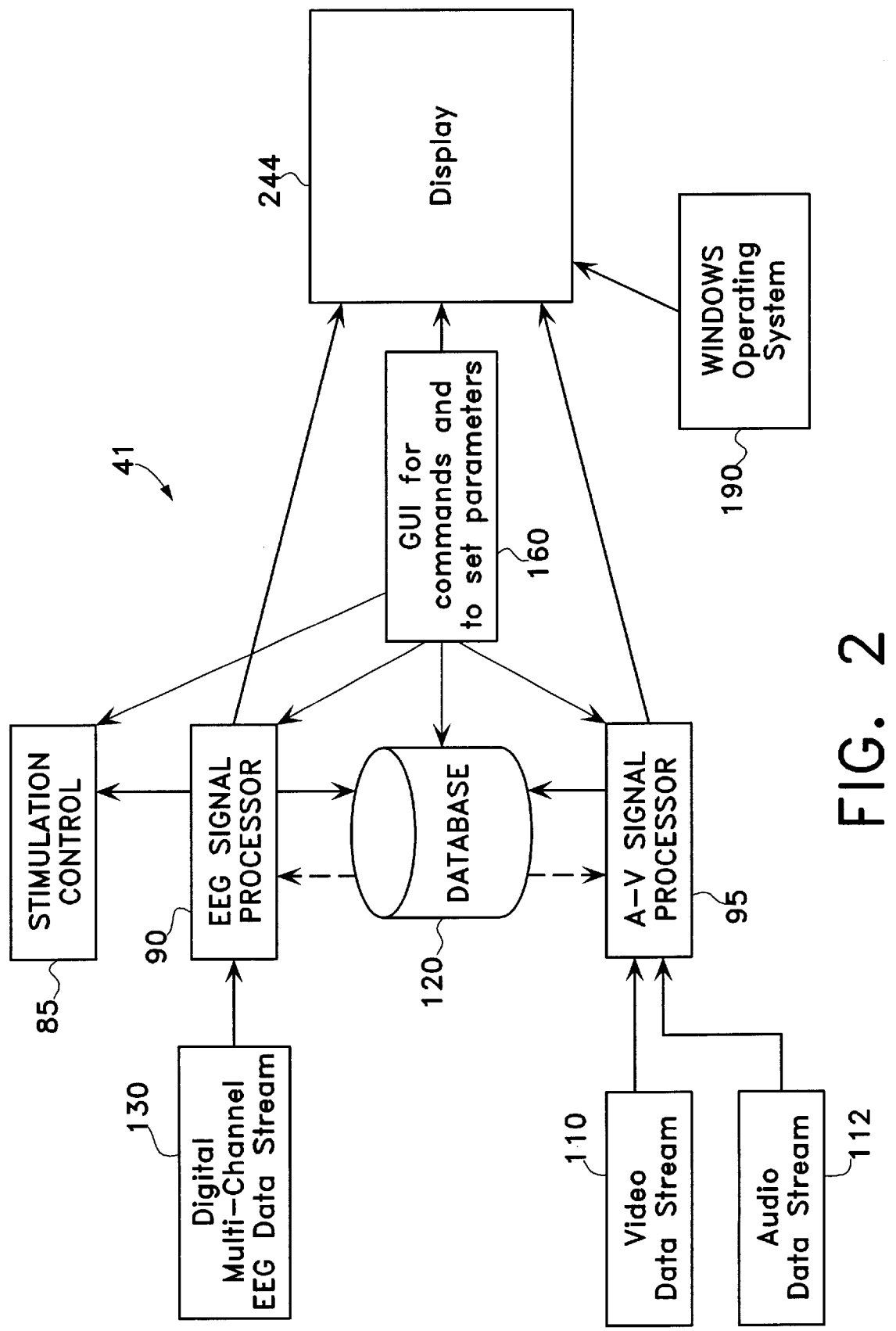
FIG. 2 is a block diagram of the system software for the physician's workstation.

FIG. 2 depicts the architecture of the system software 41 of FIG. 1.

The term "module", as used herein, refers to a unit of software code that carries out a specific function. A module may comprise processes, libraries subroutines, and other software components.

The CPU 48 of FIG. 1 receives the digital multi-channel EEG data stream 130 over the data link 43 from the amplifier system 20. The digital multi-channel EEG data stream 130 is the input data for the EEG signal processor module 90 which in turn may store and retrieve EEG data from the database 120 and display it on the display 244 as shown on the monitor 44 of the physician's workstation 40 of FIG. 1. The EEG signal processor module 90 may also send commands to the stimulation control module 85 both to start and to stop stimulation. The stimulation control module 85 controls the parameters and commands sent to external stimulation equipment such as the stimulator 30 of FIG. 1.

A video data stream 110 from the video card 47 of FIG. 1 and an audio data stream 112 from the microphone 82 of FIG. 1 is processed by the AV signal processor 95 which in turn stores and retrieves audio and video from the database 120, replays the audio, and displays the video on the display 244.

A graphical user interface (GUI) 160 provides physician control of the physician's workstation software 41 through menus and toolbars shown on the display 244. The GUI 160 may have menus and toolbars to control the EEG signal processor module 90, the stimulation control module 85, the video signal processor module 95, the database 120, and the display 244. If so desired, the display 244 may show the WINDOWS operating system 190 task bar and therefore other WINDOWS programs may be run as desired by the system user.

Figure 3:
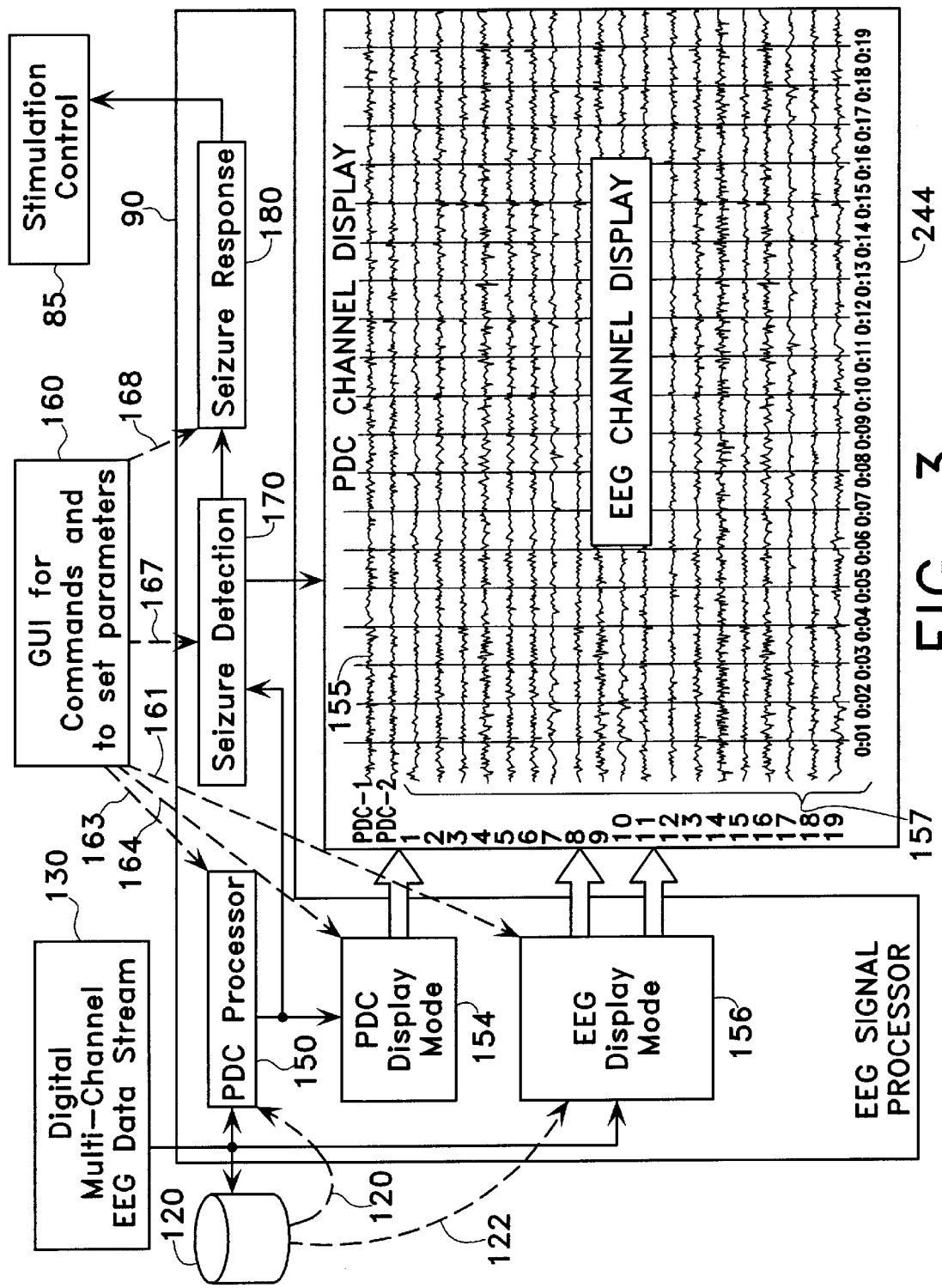
FIG. 3 is a block diagram of the EEG processing module used by the physician's workstation.

FIG. 3 shows a processing schematic for the EEG processor module 90 of the system software 41 of FIG. 2. The EEG processor module 90 may be made up of several smaller modules which together function to process, to store, to retrieve, and to display EEG signals and to detect and to respond to epileptiform activity.

The incoming digital multi-channel EEG data stream 130 is processed by three modules of the EEG processor module 90.

1. The EEG database 120 stores the real time digital multi-channel EEG data stream 130 for later retrieval from the database 120 in the form of retrieved data stream 122.
2. The EEG display mode module 156 displays the digital multi-channel EEG data stream 130 as the EEG signal display 157 on the central portion of the physician's workstation display 244 on the monitor 44 of FIG. 1.
3. The PDC processor module 150 combines, in a manner discussed elsewhere, selected channels of the digital multi-channel EEG data stream 130 to form one or more PDC's 155 (shown as "PDC-1" and "PDC-2") which are displayed by the PDC display mode module 154 on the upper part of the central section of the physician's workstation display 244. Although in the example shown in FIG. 3, only two PDC's 155 are displayed, it is within the scope of this invention that as few as one PDC or as many as 20 PDC's may be displayed, the number depending only upon the capacity of the computing and measuring equipment. In most cases one to three PDC's 155 would be sufficient.

Although the following discussion describes the present invention with respect to epileptiform activity detection, the techniques and allied devices are applicable to any detectable neurological event.

The output from the PDC processor module 150 is also processed by the neurological event detection module 170 with one or more modules to provide patient-customized detection of epileptiform activity. Detected epileptiform activity may initiate a patient customized response by the seizure response module 180, depending upon other system componentry which may be involved. In the depicted variation, detected epileptiform activity also is shown on the current display 244 and may be saved to the database 120 for future retrieval.

A Graphics User Interface (GUI) 160 may be built into the system software 41 to provide user control of the parameters and programming of the various modules discussed above.

Specifically, a desired set of parameters for each of the modules are described below. For instance, the parameters 161 for the EEG display mode module 156 may be made up of:

1. Total number of EEG channels to display.
2. Choice of which channels to show or hide.
3. Labels for each channel.
4. Amplitude gain adjustment for the display in units such as micro or millivolts.
5. The number of seconds per screen (typically from 10 seconds to two minutes.)
6. Special display modes for each EEG channel including inverted, RMS and moving average where the averaging time is an adjustable parameter.
7. Display colors including background, foreground, labels and comments for each part of the display.

Figure 4:
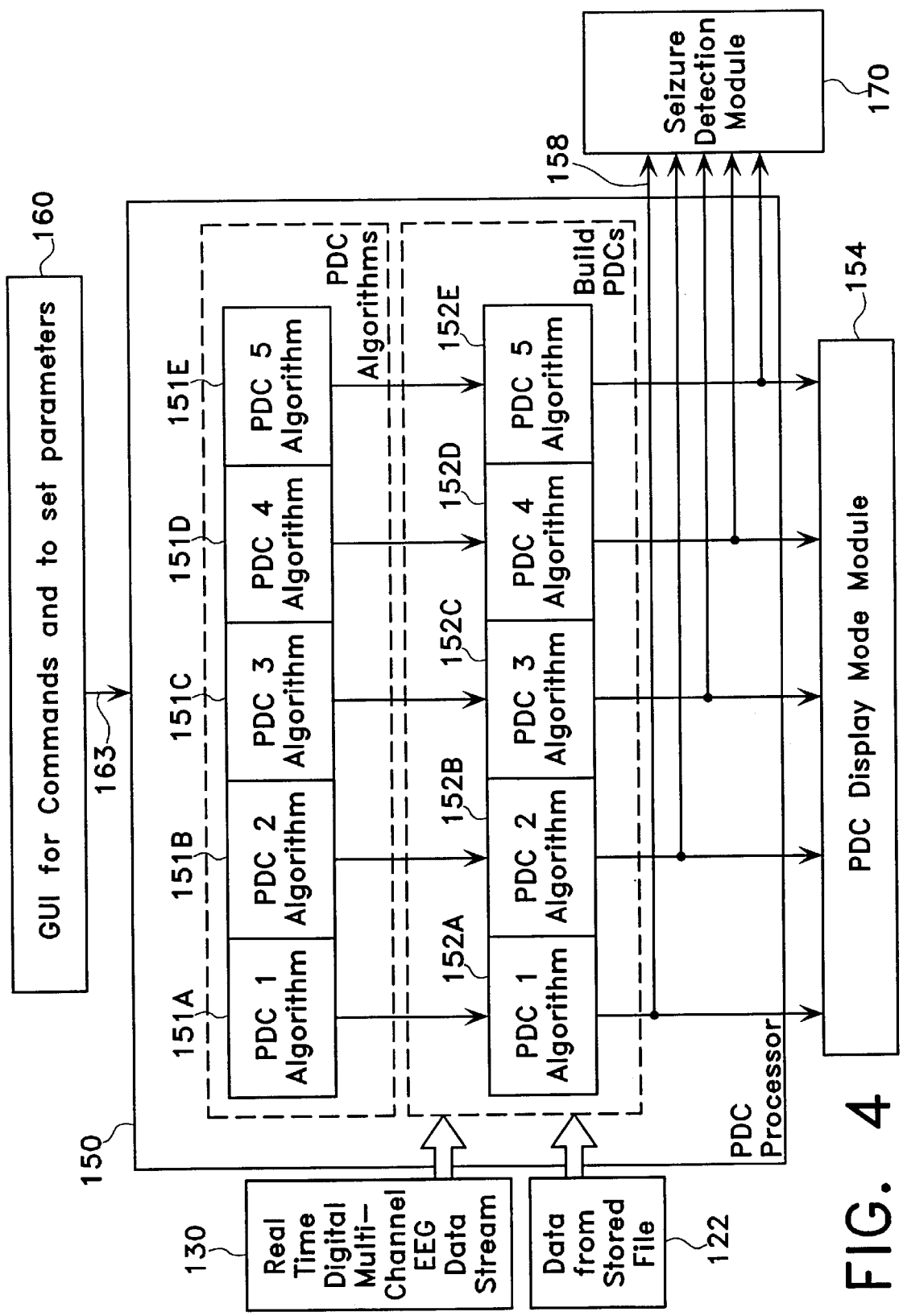
FIG. 4 depicts a block diagram of the PDC processor module of the EEG signal processor of FIG. 3

FIG. 4 depicts a block diagram of the PDC processor module 150 of the EEG signal processor 90 of FIG. 2. The data input to the PDC processor module 150 may be either the real-time digital multi-channel EEG data stream 130 or previously stored multi-channel EEG data 122 from database 122. The command and programming input 163 to the PDC processor 150 desirably comes from the GUI 160. The GUI 160 allows the algorithms 151A through 151E inclusive to be selected and programmed. The programming comprises selecting which of the EEG channels will be combined to form each PDC, whether the EEG channel selected is added or subtracted from the PDC and the format in which each PDC will be displayed on the monitor by the PDC display module 154. A weighting of each EEG channel which forms a PDC may also be used to adjust for variations in signal level, electrode sensitivity, etc.

Suitable techniques for forming a weighted sum or difference of signals are well known. Similarly, in U.S. Pat. No. 6,016,449 (which patent is incorporated by reference), Fischell et al describe the use of time delays applied to EEG signals before combining those signals. Such a technique is also applicable to PDC production.

The PDC "build" modules 152A through 152E, inclusive, individually construct the five PDC's shown in FIG. 4 according to the programs stored in the PDC algorithms 151A through 151E. Although five PDC's are here depicted, it should be understood that typically only one, two, or three PDC's would be needed. Other times, as many as 20 PDC's may be of value.

An example of a PDC algorithm 151A might sum together two or more EEG channels with the largest signal amplitude at the time of a patient's seizure. If a patient has seizures that originate in two parts of the brain but only one PDC is desired, an algorithm of merit may use the difference between the EEG channel that best shows the first site of seizure onset and the EEG channel that best shows the second site. In many cases, simply picking the single EEG channel which best shows the seizure onset may be the most appropriate PDC algorithm.

If 32 EEG channels are available for input to the PDC processor 150, examples of PDC algorithms are:

1. EEG channel 3+EEG channel 8+EEG channel 24+EEG channel 30

2. EEG channel 5–EEG channel 14

3. EEG channel 1+EEG channel 12–EEG channel 23

4. EEG channel 1+EEG channel 12–2×EEG channel 23

The algorithms 3 and 4 in the list above would be useful in subtracting out an EEG channel showing non-seizure events which also appear in the summed EEG channels 1 and 12. This would reduce the sensitivity of the system to detecting the non-seizure events. The algorithm 4 uses a weighting of 2× on the subtracted EEG channel 23 to better cancel the unwanted events with signal that is essentially doubled by the summing of EEG channels 1 and 12. It is also envisioned that high, low, notch, and bandpass filtering as are known in the art of signal processing may be part of the PDC algorithms 151A through 151E inclusive. Such filtering may utilize frequency domain transformations.

Figure 5:
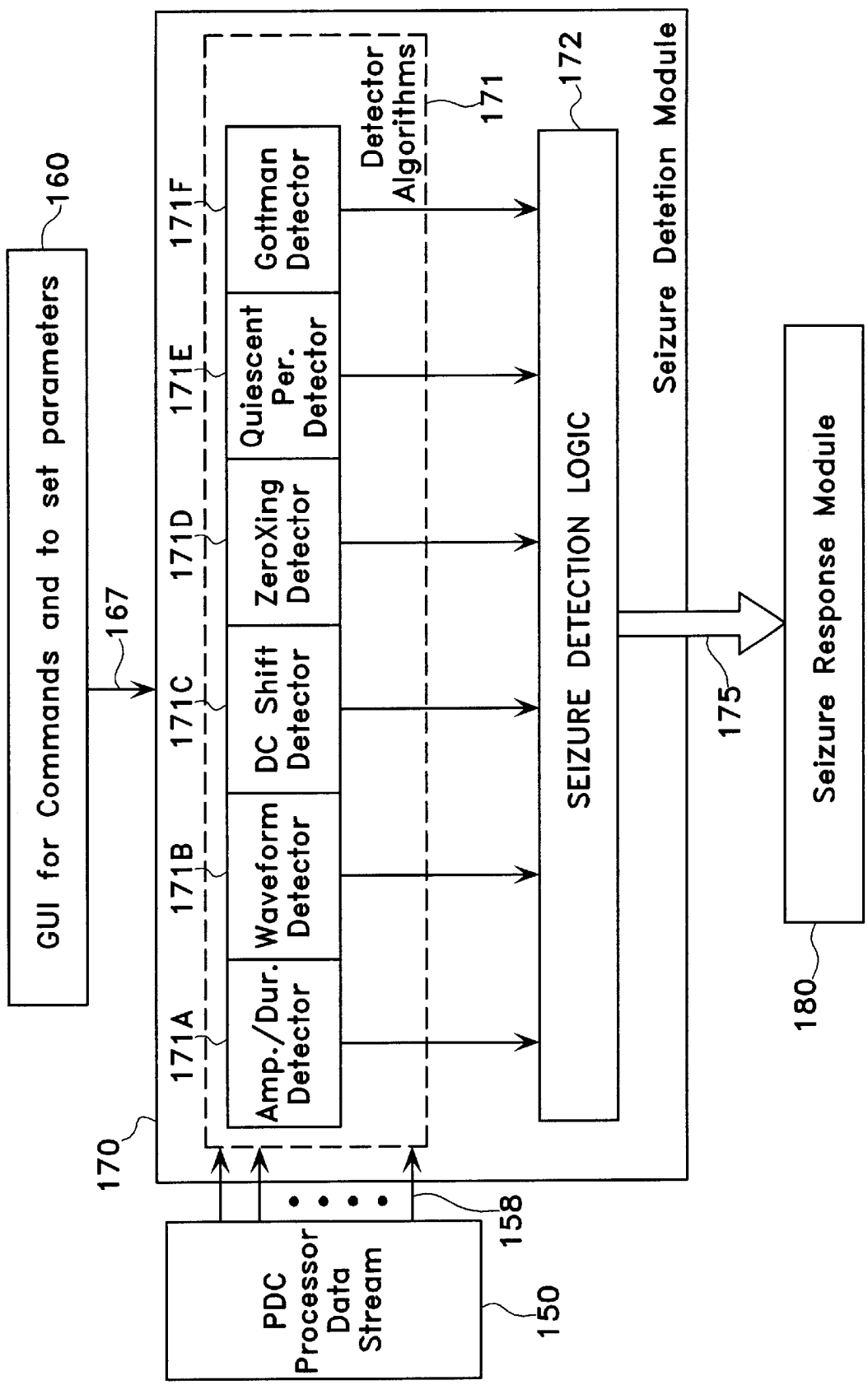
FIG. 5 depicts a block diagram of the seizure detection module of the EEG signal processor of FIG. 3.

FIG. 5 shows a block diagram of the seizure detection module 170 of the EEG signal processor 90 of FIG. 3. The seizure detection module 170 receives the PDC data streams 158 from the PDC processor 150 shown in FIG. 4. Each of the PDC data streams 158 is analyzed by one or more of the seizure detector algorithms 171 to determine if an event has occurred.

In the variation shown in FIG. 5, six different detector algorithms 171A through 171F are depicted. If so desired, the algorithms may be simultaneously implemented within the seizure detection module 170. Typically, only one or two detector algorithms at a time would be enabled on a particular PDC. The six detector algorithms 171A through 171F are described further with relation to FIGS. 6, 7, 8, 9, 10, and 11.

Specifically, the desired detection algorithms are an amplitude duration detector 171A, a waveform detector 171B, a DC shift detector 171C, a zero crossing detector 171D, a quiescent period detector 171E, and a Gotman algorithm detector 171F. Although the same detector algorithms may be used on each of the PDC's; it is equally possible that chosen detector algorithms for each PDC be completely different. The Gotman algorithms have been published and are well known in the art of seizure detection algorithms; see, for instance, "Automatic Detection of Seizures and Spikes" Jean Gotman, Journal of Clinical Neurophysiology, 16(2):13–140, 1999.

When an event is detected on any PDC by the enabled detector algorithms, the result (yes or no) is sent to the seizure detection logic 172 that allows sophisticated logic to be applied when multiple PDC's are being used. The seizure detection logic 172 sends out a "seizure detected" signal 175 to the seizure response module 180 when a set of logical conditions are met. Such logic includes the use of standard Boolean functions such as "and", "or", and "not" to be used together or separately to further resrict the conditions for a valid seizure detection. The three examples of logical conditions, listed below, are set by commands and downloaded system parameters 167 from the GUI 160 to the seizure detection module 170. They are:

a. Seizure activity is detected in every PDC within a set period of time.

b. Seizure activity is detected in any PDC.

c. Seizure activity must be present in a first PDC but must not be present in a second PDC. This is useful to disallow certain patterns similar to epileptiform activity such as sleep spindles from setting off the detector.

More complex logic used with more than two PDC's may also be employed.

If electrical stimulation is to be used to respond to a detected seizure, the seizure response module 180 will signal the stimulation control module 85 of FIG. 2 to initiate appropriate stimulation. The seizure response module 180 desirably also stores the time and date of the detection and causes the actual and specific EEG channel data to be saved to the database 120 seen in FIG. 2. By using standard buffering techniques, the stored EEG data may comprise EEG channel data from some time before the seizure detection by the seizure detection module 170.

Each of the detectors 171A through 171F preferably internally resets itself after a valid seizure detection event. This internal reset may prohibit a subsequent detection for a specific time period.

Figure 6:
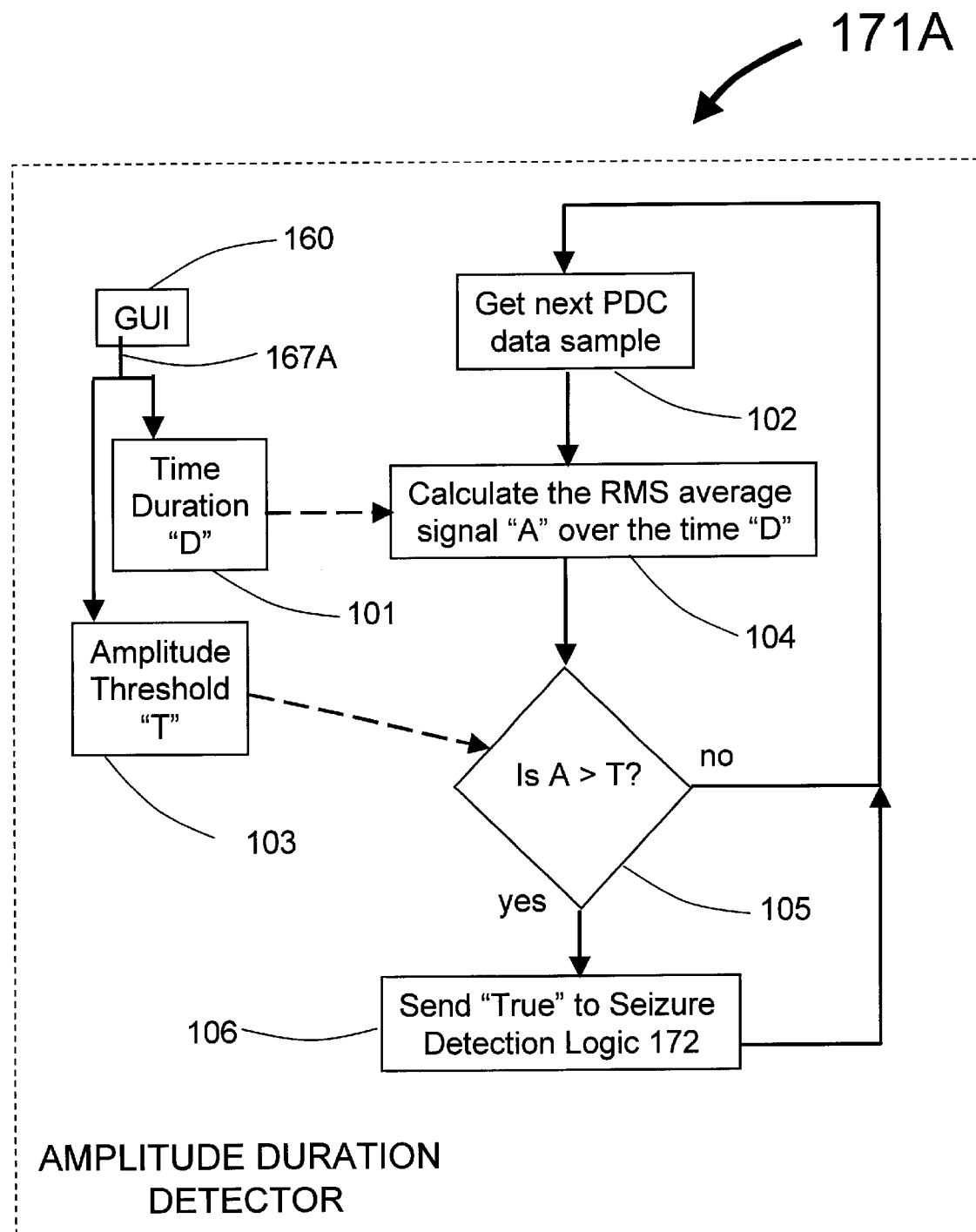
FIG. 6 depicts a block diagram of the amplitude duration detection algorithm.

FIG. 6 shows a block diagram of the amplitude duration detection algorithm 171A which compares the average Root Mean Squared (RMS) amplitude "A" in a PDC over a time duration "D" 101 to a threshold "T" 103. Both the time duration "D" 101 and the threshold "T" 103 are together the amplitude duration detection parameters 167A that are input to the amplitude detection algorithm 171A from the GUI 160. The amplitude duration detection algorithm 171A functions as follows:

a. The process 102 gets the next data sample from the PDC.

b. The process 104 calculates the average RMS signal level "A" over the time duration "D" 101 which is the sample from the process 102 retrieved in step 1 above.

c. The process 105 compares the average RMS signal level "A" over the time duration "D" 101 with a pre-set threshold "T" 103. If the value of "A" is greater than "T", then an event is "declared" and the process 106 sends a "True" signal to the Seizure Detection Logic 172 of FIG. 5. If no "True" signal is sent to the Seizure Detection Logic 172 block, the algorithm returns to process 102 to get the next sample from the PDC.

Figure 7:
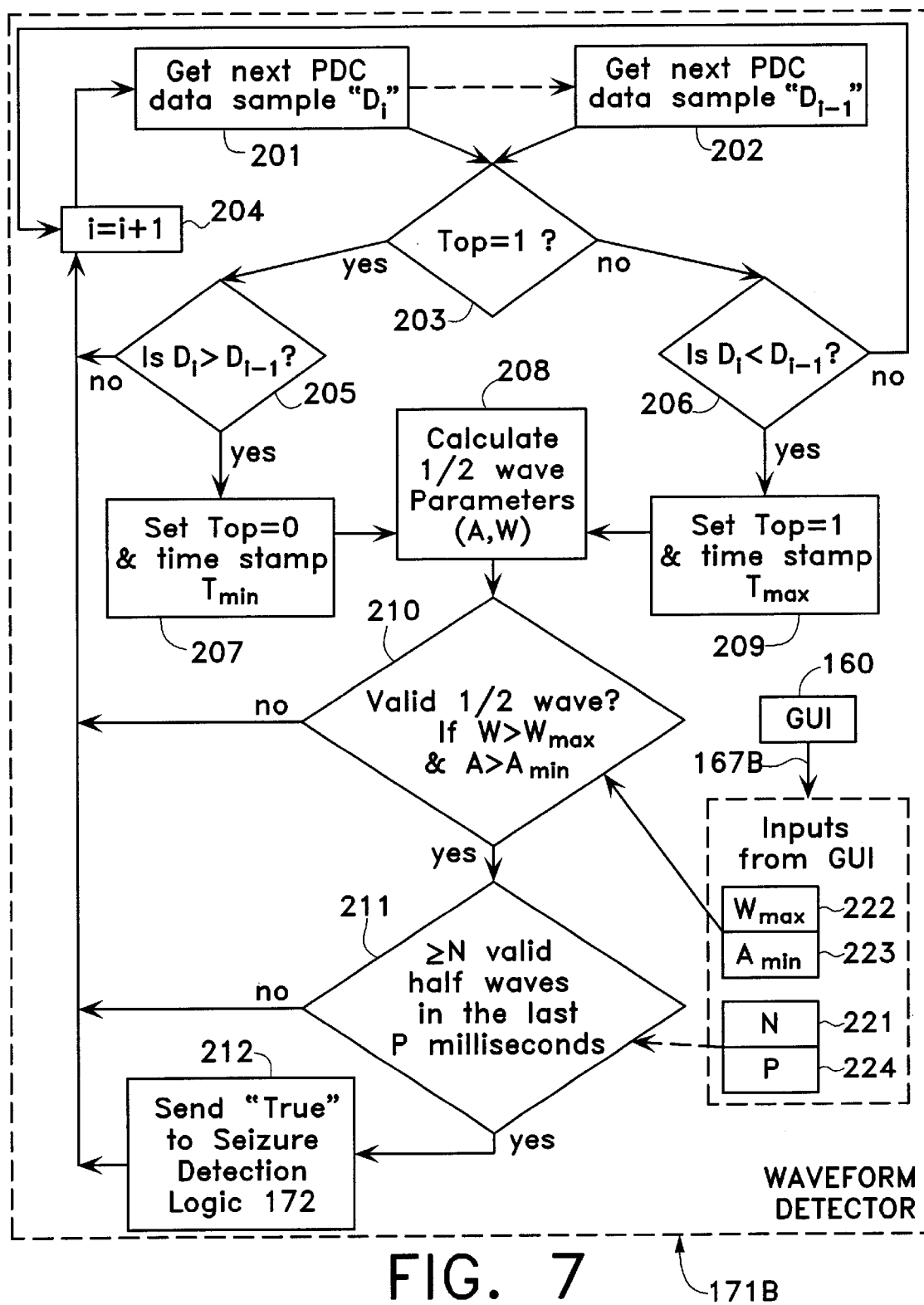
FIG. 7 depicts a block diagram of a waveform detector.

FIG. 7 shows a block diagram of a waveform detector algorithm 171B which determines if there have been at least "N" 221 half waves that are at least "$W_{min}$" 222 long and of at least "$A_{min}$" 223 peak-to-peak amplitude over the period "P" 224. Taken together, the parameters "N" 221, "$W_{min}$" 222, "$A_{min}$" 223, and "P" 224 are waveform detection parameters 167B that are introduced to the amplitude detection algorithm 171B from the GUI 160. The depicted waveform detection algorithm 171B functions as follows:

1. The process 201 gets the next data sample "$D_i$" from the PDC.

2. Sample value "$D_i$" is sent to the process 202 to hold for comparison when the next sample is taken. At the time the sample "$D_i$" is sent to the process 201, the process 202 holds the previous sample "$D_{i-1}$".

3. Both "$D_i$" and "$D_{i-1}$" are passed to the process 203 that looks at the register Top that is set on the basis of whether the last signal peak was a maximum or a minimum. If it was a maximum the register Top is 1, if it was a minimum, the register Top is 0.

a. If Top=1 then the process 205 is run to check if the sample "$D_i$" is greater than the sample "$D_{i-1}$" (i.e. if the waveform which had previously been at a maximum has reached a minimum and started up again).

i. If "$D_i$">"$D_{i-1}$" then the sample "$D_{i-1}$" was a minimum (or bottom) in the waveform and the following will occur:

I. Top will be set to 0 by the process 207 to indicate that the last peak was a maximum. The process 207 will also time stamp (i.e. save the time of occurrence "$T_{min}$") of the minimum.

II. Half wave parameters are then calculated by the process 208. These comprise the half wave width "W", peak-to-peak amplitude "A" from the previous saved maximum at time=$T_{max}$ to the just detected minimum (sample "$D_{i-1}$") at time=$T_{min}$.

III. Once the half wave parameters are calculated by the process 208 the algorithm is ready to check for a valid waveform and proceeds to step 4.

ii. If "$D_i$" is not >"$D_{i-1}$", then a minimum has not yet been reached and the next PDC data sample is obtained by process 201 after i=i+1 is set by the process 204 (i.e. the counter "i" is incremented by one to get the next PDC data sample).

b. If Top=0 then the process 206 checks if the sample "$D_i$" is less than the sample "$D_{i-1}$" (i.e. if the waveform which had previously been at a minimum has reached a maximum and started down again). If "$D_i$"<"$D_{i-1}$" then the sample "$D_{i-1}$" was a maximum (or top) in the waveform and the following will occur:

I. Top will be set to 1 by the process 209 to indicate that the last peak was a maximum. The process 209 will also time stamp (i.e. save the time of occurrence "$T_{max}$") of the maximum.

II. Half wave parameters are then calculated by the process 208. These comprise the half wave width "W", peak-to-peak amplitude "A" from the previous saved minimum at time=$T_{min}$ to the just detected maximum (sample "$D_{i-1}$") at time=$T_{max}$.

III. Once the half wave parameters are calculated by the process 208 the algorithm is ready to check for a valid waveform and proceeds to step 4.

ii. If "$D_i$" is not <"$D_{i-1}$" then a maximum has not yet been reached and the next PDC data sample is obtained by process 201 after i=i+1 is set by the process 204 (i.e. the counter i is incremented by one to get the next PDC data sample).

4. The process 210 then checks to see if the half wave is valid. A valid half wave is one that has a wave width "W" that is greater than the minimum wave width "$W_{min}$" 222 and a larger peak-to-peak amplitude "A" than the minimum peak-to-peak amplitude "$A_{min}$" 223.

a. If either of these conditions are not met ("W">"$W_{min}$" and "A">"$A_{min}$") then the half wave is not valid and the next PDC data sample is obtained by process 201 after i=i+1 is set by the process 204 (i.e. the counter i is incremented by one to get the next PDC data sample).

b. If both "W">"$W_{min}$" and "A">"$A_{min}$" then the algorithm continues to check if there have been at least "N" 221 valid half waves in the period "P" 224.

i. If there have not been at least "N" 221 valid half waves in the last "P" 224 seconds (or other suitable selected periods of time) then the next PDC data sample is obtained by process 201 after i=i+1 is set by the process 204 (i.e. the counter i is incremented by one to get the next PDC data sample).

ii. If there have been at least "N" 221 valid half waves in the last P 224 seconds then the "True" event detection is sent to the Seizure Detection Logic block 172 by the process 212 and then the next PDC data sample is obtained by process 201 after i=i+1 is set by the process 204 (i.e. the counter i is incremented by one to get the next PDC data sample).

Although the depicted waveform detector 171B uses as inputs, the half wave parameters 221, 222, 223 and 224 as shown in FIG. 7, it may be desirable to input the parameters for the waveform detector 171B in terms of full waves rather than half waves. Full waves are easier to estimate by eye since only the number of maximums in the signal over a given period of time need be counted. Further, full wave parameters may in any event, be converted to half wave parameters by the GUI 160. In this way, the input parameters 167B to the waveform detector algorithm 171B would always be in half waves.

Obviously, when using full wave input, the full wave parameters would be the number of full waves "$N_{fw}$" of minimum full wave width "$W_{fwmin}$" and minimum amplitude "$A_{min}$" 223 in the period "P" 224. Note that the amplitude and period do not change in going from half to full waves. The relationship between full wave parameters and the half wave parameters are as follows:

$N = 2 \times N_{fw}$ $W_{min} = \frac{1}{2} \times W_{fwmin}$

The process steps 210 and 211 may be used to convert between half and full wave parameters.

The waveform detector algorithm has the advantage of being well suited to the detection of the precursor to a seizure as recorded from intracranial electrodes. For a given patient, these precursors tend to have the same waveform pattern before every seizure. The example described herein to implement a waveform detector is one of many ways to detect waveforms with specific amplitude and frequency characteristics. For example, one could accept half waves with wave duration "W">"$W_{min}$" and require both that the number of half waves "N" in a time period "P" be greater than or equal to "N" and the average amplitude of all half waves during the time period "P" be greater than "$A_{min}$". This differs from the algorithm 171B of FIG. 7 which checks the amplitude of each half wave rather than requiring a minimum average amplitude over a period of time.

In an additional variation, the waveform detector is used to combine any pair of half waves both of which are of short duration and low amplitude below a preset threshold with the previous half wave. This approach eliminates small glitches or notches in the signal. Alternatively, low pass filtering may be used to accomplish the same result.

Figure 8:
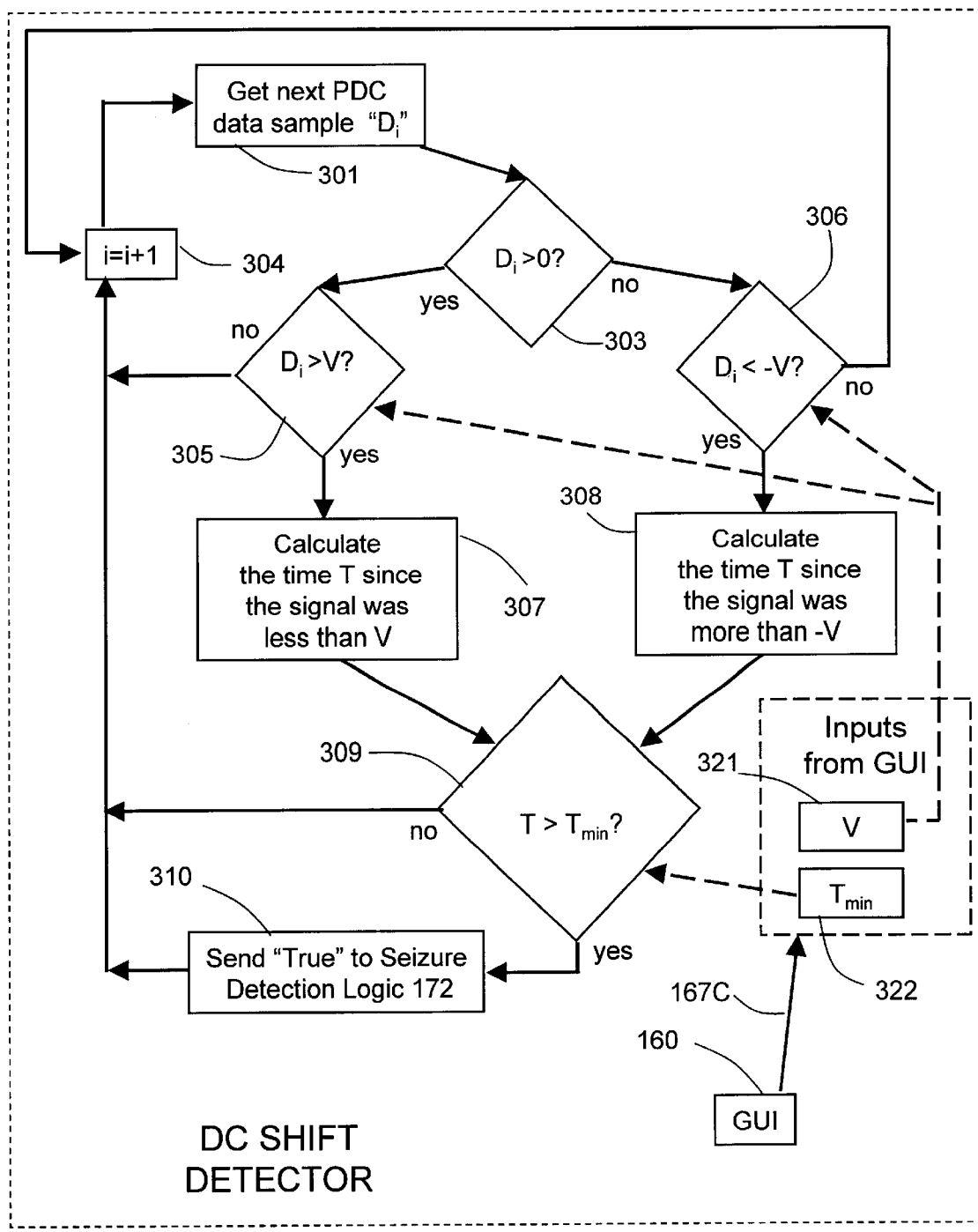
FIG. 8 depicts a block diagram of a D.C. shift detector.

FIG. 8 shows a block diagram of a DC shift detector algorithm 171C that looks for a DC signal with amplitude larger than a threshold "V" 321 for a minimum time "$T_{min}$" 322. This means that the signal must remain greater than +V for a minimum time "$T_{min}$" or less than -V for a minimum time "$T_{min}$". The parameters "V" 321 and "$T_{min}$" 322 are together the DC shift detector parameters 167C which are input to the amplitude detection algorithm 171C from the GUI 160. The depicted DC shift detector algorithm 171C functions as follows:

1. The process 301 gets the next data sample "$D_i$" from the PDC and passes it to the process 303 which checks as to whether the data sample is positive or negative.

a. If the data sample "$D_i$" is positive (>0) the process 305 checks if "$D_i$" is greater than "V" 321 as follows:

i. If "$D_i$" is not greater than the "V" 321, then there is not a valid DC shift and the next PDC data sample is obtained by process 301 after i=i+1 is set by the process 304 (i.e. the counter i is incremented by one to get the next PDC data sample).

ii. If "$D_i$" is greater than "V" 321, then the time "T" since the signal was last less than "V" 321 is calculated by the process 307 and the algorithm goes to process 309 described in step 2. that follows.

iii. If the data sample "$D_i$" is not positive (<0) the process 306 checks to determine whether "$D_i$" is less than −V 321 as follows:

iv. If "$D_i$" is not less than −V 321, then there is not a valid DC shift and the next PDC data sample is obtained by process 301 after i=i+1 is set by the process 304 (i.e. the counter i is incremented by one to get the next PDC data sample).

v. If "$D_i$" is less than −V 321, then the time "T" since the signal was last greater than −V 321 is calculated by the process 307 and the algorithm goes to process 309 described in step 2. which follows.

2. Process 309 checks if the time "T" is greater than the minimum time "$T_{min}$" required to detect a valid DC shift.

a. If "T" is not greater than "$T_{min}$" then the DC signal has not been sufficient in length beyond the threshold to detect a valid DC shift. The next PDC data sample is then obtained by process 301 after i=i+1 is set by the process 304 (i.e. the counter i is incremented by one to get the next PDC data sample).

b. If "T" is greater than "$T_{min}$" then a there is a valid DC shift and the process 310 sends a "True" seizure detection indication to the Seizure Detection Logic block 172 of FIG. 5. Then, the next PDC data sample is obtained by process 301 after i=i+1 is set by the process 304 (i.e. the counter i is incremented by one to get the next PDC data sample).

An alternate embodiment of the DC shift detector uses a "not to exceed threshold" value "$V_n$" which defines a more limited DC range that must be between "V" and "$V_n$" for the minimum time "$T_{min}$" to indicate a neurological event for the purposes of this invention.

Figure 9:
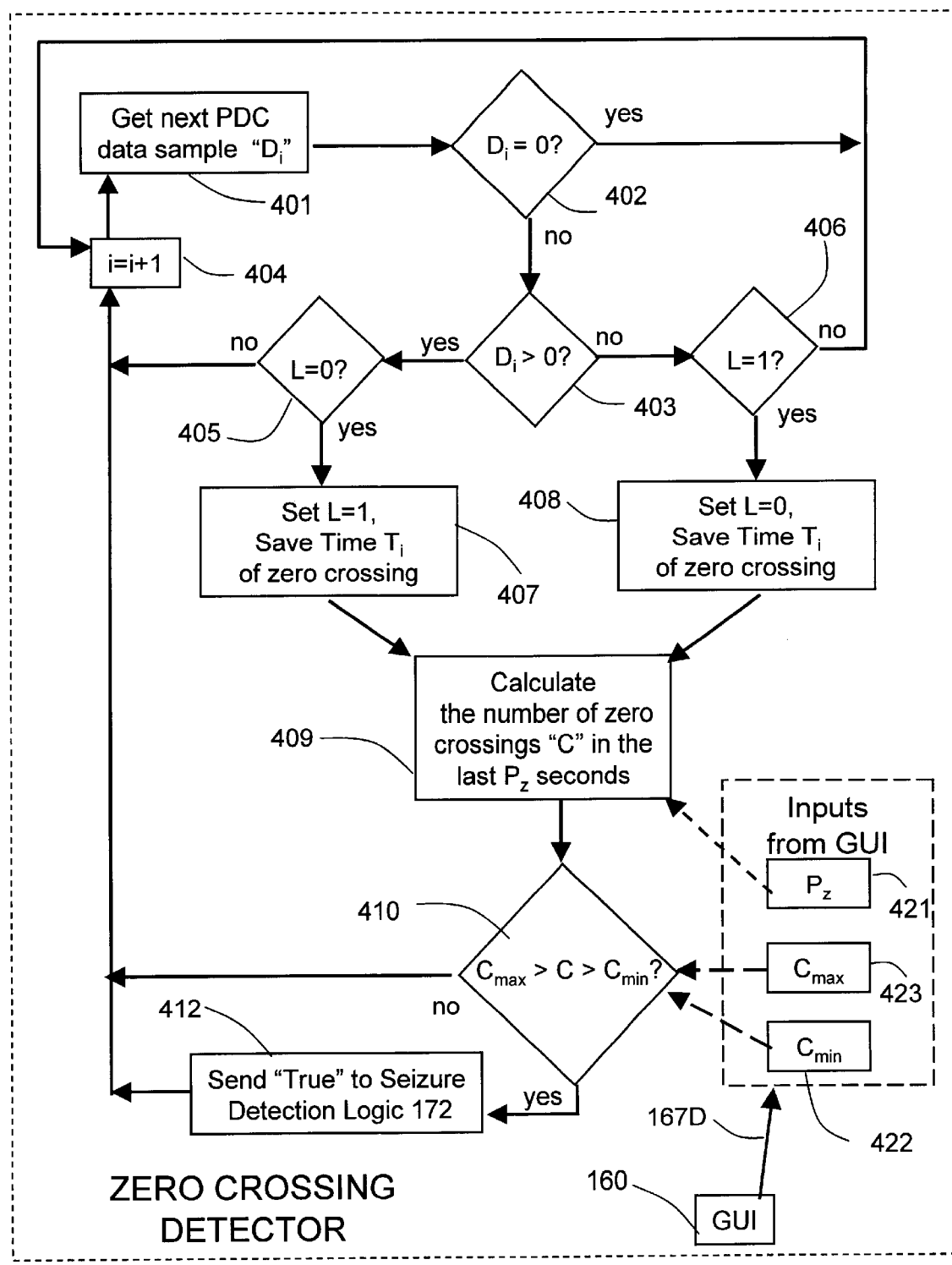
FIG. 9 depicts a block diagram of a zero crossing detector.

FIG. 9 shows a block diagram of a zero crossing detector 171D which counts the number of times "C" in a period $P_z$ 421 that the PDC signal crosses the zero axis (i.e. how many times does the signal go from positive to negative or negative to positive). The algorithm 171D compares the number of counted zero crossings "C" with the maximum and minimum required zero crossings "$C_{max}$" 423 and "$C_{min}$" 422. The parameters "$P_z$" 421, "$C_{max}$" 423, and "$C_{min}$" 422 are together the zero crossing detector parameters 167D which are input to the zero crossing algorithm 171D from the GUI 160. The depicted zero crossing detector algorithm 171D functions as follows:

1. The process 401 gets the next data sample $D_i$ from the PDC and passes it to the process 402 which checks as to whether the data sample is zero (neither positive or negative).

a. If $D_i=0$, then zero has not been crossed and the next PDC data sample is obtained by process 401 after i=i+1 is set by the process 404 (i.e. the counter i is incremented by one to get the next PDC data sample).

b. If "$D_i$" is not zero, then go to process 403 to determine if "$D_i$" is positive or negative.

i. If the data sample "$D_i$" is positive the process 405 checks if the last non-zero sample was positive or negative. The register "L" is used to indicate this by L=1 if the last non-zero sample was positive and L=0 if the last non-zero sample was negative.

I. The process step 405 checks whether L=0. If "L" is not zero, that means that the last non-zero sample was positive and since the current sample is positive, zero has not been crossed and the next PDC data sample is obtained by process 401 after i=i+1 is set by the process 404 (i.e. the counter i is incremented by one to get the next PDC data sample).

II. The process step 405 checks whether L=0. If L=0, that means that the last non-zero sample was negative and since the current sample is positive, the PDC value has crossed zero and the process 407 is run to change "L" to equal 1 and to save the time "$T_i$" of the zero crossing. The Zero Crossing Detection algorithm 171D then goes to process 409 as described in step 2 which follows below.

ii. If the data sample "$D_i$" is negative, the process 406 checks whether the last non-zero sample was positive or negative. The register "L" is used to indicate whether the last non-zero sample was positive or negative, i.e., L=1 if the last non-zero sample was positive and L=0 if the last non-zero sample was negative. The process 406 checks if L=1.

I. If L is not equal to 1 that means that the last non-zero sample was negative and since the current sample is negative, zero has not been crossed and the next PDC data sample is obtained by process 401 after i=i+1 is set by the process 404 (i.e. the counter i is incremented by one to get the next PDC data sample).

II. If L=1, then the last non-zero sample was positive and since the current sample is negative, zero has been crossed and the process 408 is run to set "L" to 0 and to save the time "$T_i$" of the zero crossing. The Zero Crossing Detection Algorithm 171D then goes to process 409 as described in step 2 that follows.

2. The process step 409 calculates the number of zero crossings "C" occurring over the time period "$P_z$".

3. The Zero Crossing Detection Algorithm 171D then runs process 410 to determine if the number of zero crossings "C" is greater than or equal to the minimum required zero 25 crossings "$C_{min}$" 422 introduced from the GUI 160.

a. If "C" is not between "$C_{min}$" and "$C_{max}$" then there has not been a valid zero-crossing-based seizure detection and the next PDC data sample is obtained by process 401 after i=i+1 is set by the process 404 (i.e. the counter i is incremented by one to get the next PDC data sample).

c. If "C" is between than "$C_{min}$" and "$C_{max}$" then there has been a valid zero-crossing-based seizure detection, the process 412 sends a "True" seizure detection indication to the seizure detection logic 172 of FIG. 5.

5. Then the next PDC data sample is obtained by process step 401 after i=i+1 is set by the process step 404 (i.e. the counter i is incremented by one to get the next PDC data sample).

An additional step may be added in the process 410, i.e., for comparing the average amplitude of the signal maximums and minimums (tops and bottoms) which occur between the zero crossings and requiring that they be greater than a specific threshold value in order to have a valid detection.

Figure 10:
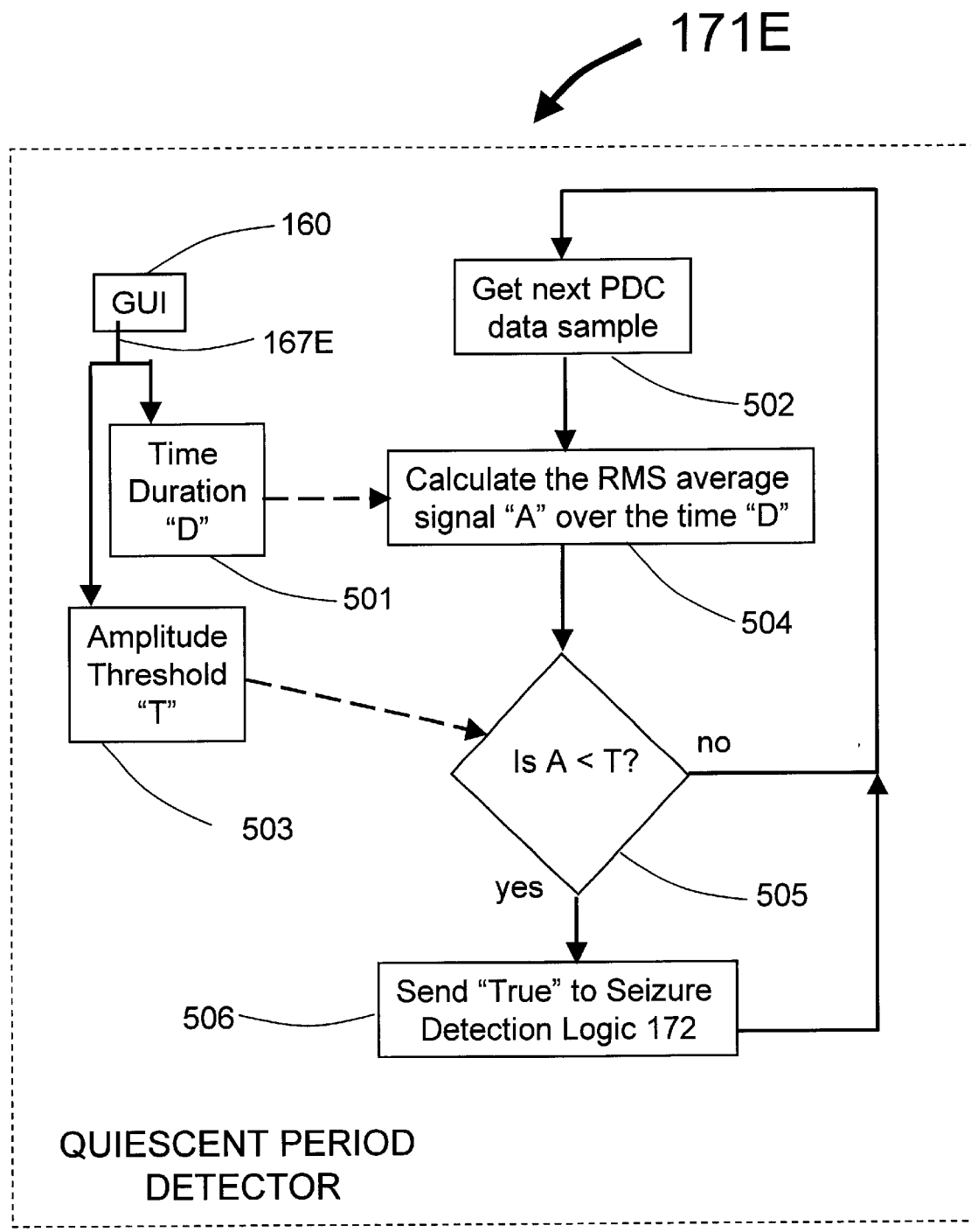
FIG. 10 depicts a block diagram of a quiescent period detector.

FIG. 10 shows a block diagram of a Quiescent Period Detector Algorithm 171E which algorithm monitors for a reduction in the PDC's average RMS signal level below a threshold "T" 503 over a time duration "D" 501. Both of the time quiescent period detection parameters 167E are introduced to the Quiescent Period Detector Algorithm 171E from the GUI 160. The depicted Quiescent Period Detector Algorithm 171E functions as follows:

1. The process 502 gets the next data sample from the PDC.
2. The process 504 calculates the average RMS signal level "A" over a time duration "D" 501 which comprises the sample from the process 502 retrieved in step 1 above.
3. The process 505 compares the average RMS signal level "A" over a time duration "D" 501 with a pre-set threshold "T" 503. If A<T then an event is "declared" and the process 506 sends a "True" signal to the Seizure Detection Logic 172 of FIG. 5. If this is not the case, the algorithm returns to process 502 to get the next sample from the PDC.

Figure 11:
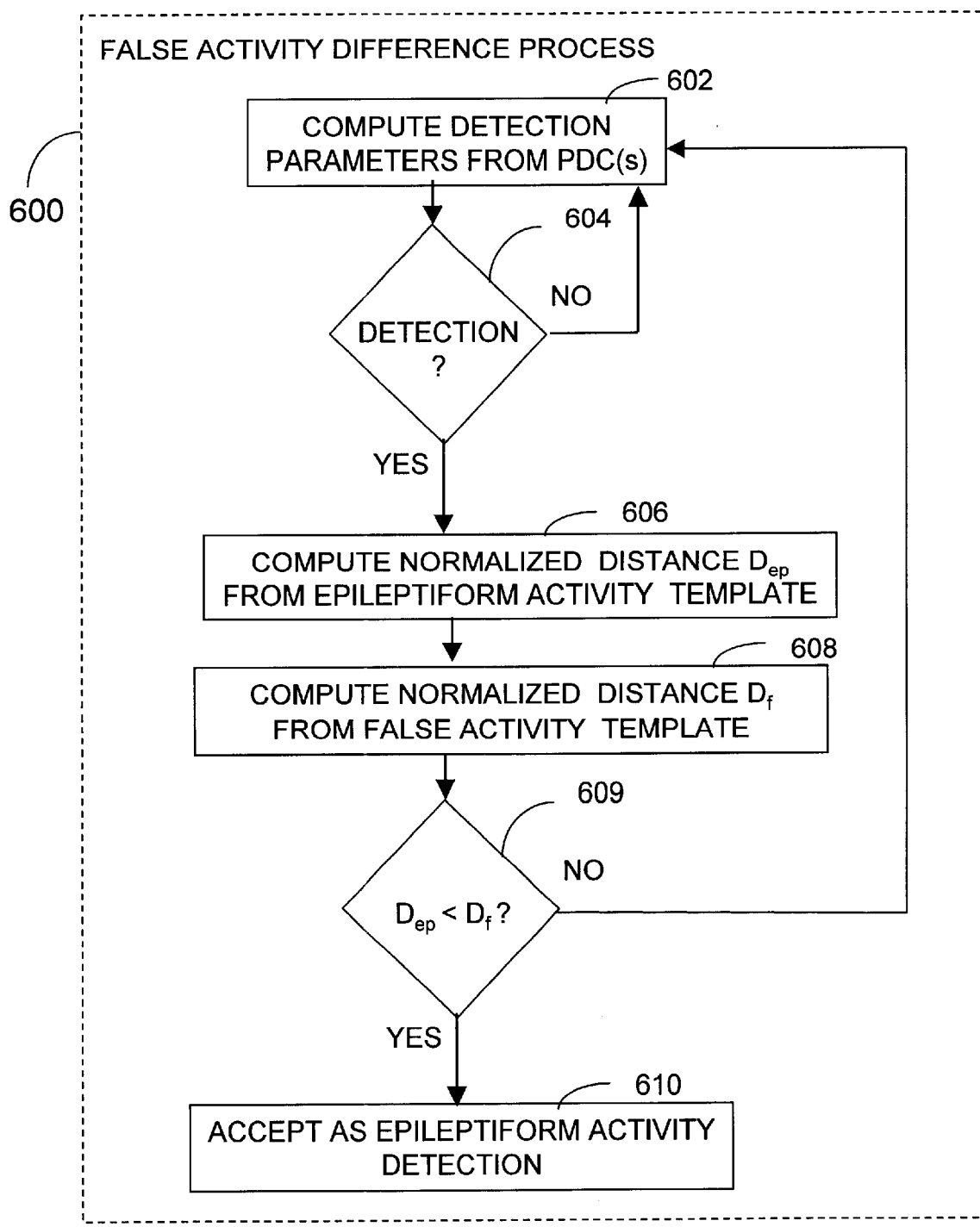
FIG. 11 depicts a block diagram of the False Activity Difference Process used to differentiate neural EEG activity that closely resembles epileptiform activity.

FIG. 11 depicts a block diagram of the False Activity Difference Process 600 used to differentiate between neural EEG activity which closely resembles epileptiform activity and true epileptiform activity.

The process begins with steps 602 and 604 where a PDC-based detection algorithm is used to detect epileptiform activity. The use of the process shown in FIG. 11 assumes that a template for detecting epileptiform activity has been previously created by analysis of the patient's prior EEG activity associated with electrographic or clinical seizures.

To prevent false epileptiform detections from false electrical activity such as sleep spindles or gamma waves, a second template must be created to detect each "false" activity of interest. In FIG. 11 only one false activity template is assumed although the process can be expanded to include multiple false templates. Following the detection 604, the normalized distance "$D_{ep}$" of the detection parameters extracted from the PDC in step 602 from the epileptiform activity template is computed in step 606. The normalized distance "$D_f$" of the detection parameters extracted from the PDC in step 602 from the false activity template is then computed in step 608. If the $D_{ep} < D_f$ (i.e. the signal is closer to epileptiform activity than the false activity) then the detection is accepted as valid epileptiform activity.

There are many well know ways to compute normalized distances between parameter sets. One such example is to compute the difference of each variable parameter from the template value as a percentage of the template value. These percentages are then added together to get a normalized distance. For example, using the waveform detector of FIG. 7 with parameters "A", "W", "N", and "P" with the template having $A_{min}$=100 microvolts, $W_{min}$=40 ms, N=8 and P=1 second, the PDC signal may be reviewed in one second segments where the variable parameters are "A", "W" and the number of half waves "Nw". If the measured parameters for a one second PDC segment are A=120 microvolts, W=44 ms and Nw=10 valid half waves, then the distance may be computed as follows:

A is 20% more than $A_{min}$,
W is 10% above $W_{min}$ and
Nw is 25% above N.
Adding the percentages of 20, 10, and 25 together gives a distance of 55.

Another technique for creating normalized distances involve summing the squares of the differences and optionally taking the square root of the result.

The features from each PDC may then be compared against a number of parameter sets (templates) from each algorithm wherein each parameter set is adjusted to detect different neurological events (e.g. onset of epileptiform activity, in-seizure epileptiform activity, sleep spindles, gamma waves, etc.). It then becomes possible for the software in an implanted device to analyze an EEG segment from the PDC's and evaluate in a quantitative fashion how similar the EEG segment is to a variety of neurological events.

For example, an exemplified EEG segment may satisfy the detection requirements both for epileptiform activity and for sleep spindles if the two events have similar morphologies within an individual patient. In such an instance, it is desirable to determine which template is a closer fit for the EEG segment. Such a discrimination may be performed in a variety of mathematical ways: e.g., by weighting the importance of each parameter in the algorithm and then summing the differences between the measured EEG characteristics and the corresponding template parameters for epileptiform activity and sleep spindles. The smaller sum is used to select the appropriate corresponding template and hence the diagnosis for the EEG segment.

This example used sleep spindles as an event which might cause a false epileptiform detection, but any confounding EEG signal which is similar in morphology to epileptiform activity may also have improved discrimination by this technique. In some cases, an initial template match might not discriminate between epileptiform activity and a sleep spindle (or other EEG signal segment similar to epileptiform activity). If analysis of the EEG segment shows that the EEG segment is essentially equally similar to both templates, the invention herein preferably provides the option to delay detection for a period of time (typically 300 to 1500 milliseconds). In so doing the temporal progression of the EEG activity is monitored to improve detection specificity. This additional spatio-temporal aspect of the detection algorithm takes advantage of the observation that epileptiform activity spreads to different electrodes at a different rate and with a different progression than does other neurological events in the same patient.

The above mentioned seizure detection system is also well suited to implementation in an implantable electrical stimulation therapy device such as a "neuropacemaker". Any or all of the above algorithms may be implemented in the neuropacemaker system described by Fischell in U.S. Pat. No. 6,016,449. The Fischell et al. document also contains description of capabilities for downloading detection algorithms from a physician's workstation to an implantable neuropacemaker.

In clinical practice, a physician's workstation 10 such as is shown in FIG. 1 would be used to diagnose and test seizure detection and stimulation algorithms for efficacy in stopping epileptiform activity before a neuropacemaker implantation procedure. According to the present invention, the effective processed-display-channel-based seizure detection algorithms may be transmitted from the physician's workstation 10 to an implantable neuropacemaker.

Although much of the description of the present invention has involved the detection of epileptiform activity, the disclosed technology is equally applicable to any neurological event that might be detectable from electrical signals received from a patient's brain. Examples of other events include the onset of Parkinson's tremors, migraine headaches, and fits of depression.

Various other modifications, adaptations, and alternative designs are, of course, possible in light of the above teachings. Therefore, it should be understood at this time that within the scope of the appended claims the invention might be practiced otherwise than as specifically described herein.

We claim as our invention:

1. A device for detection of neurological event activity in a patient's brain comprising:
   at least one brain electrode configured to monitor brain electrical signals and produce an output, each said brain electrode being positionable to a position relative to a patient's brain,
   at least one processed display channel processor configured to produce at least one processed display channel, said at least one processed display channel being a signal produced by signal processing by said at least one processed display channel processor, of a digital signal related to said output from said at least one brain electrode, the signal processing having one or more parameters;
   a neurological event detector configured to process the at least one processed display channel with at least one detector algorithm to detect neurological event activity based upon i.) the brain electrical signals received by the at least one brain electrode, ii.) the position of each brain electrode, iii.) the parameters of the signal processing used to create the at least one processed display channel, iv.) and at least one detector algorithms having at least one detector parameter customizeable for each patient.

2. The device of claim 1 wherein said at least one brain electrode is configured to accept electrical stimulation signals for the patient's brain.

3. The device of claim 1 further comprising conductors to carry electrical signals to and from the at least one brain electrode.

4. The device of claim 1 further comprising an amplifier configured to amplify the electrical signals from the at least one brain electrode to produce at least one amplified electrical signal.

5. The device of claim 4 further comprising an analog-to-digital converter configured to convert the at least one amplified electrical signal to produce said at least one digital signal.

6. The device of claim 1 wherein the neurological event activity is epileptiform activity.

7. The device of claim 1 further comprising a signal processor for the signal processing of said one or more of the digital signals to produce a processed display channel by low pass filtering.

8. The device of claim 1 further comprising a signal processor for the signal processing of said one or more of the digital signals to produce a processed display channel by high pass filtering.

9. The device of claim 1 further comprising a signal processor for the signal processing of said one or more of the digital signals to produce a processed display channel by bandpass filtering.

10. The device of claim 1 further comprising a signal processor for the signal processing of said one or more of the digital signals to produce a processed display channel by the summing of two or more of the digital signals each digital signal multiplied by a weighting factor.

11. The device of claim 1 further comprising a signal processor for the signal processing of one or more of the digital signals to produce a processed display channel by the subtraction of at least one of the digital signals from another.

12. The device of claim 11 wherein in said subtraction of at least one of the digital signals from another, each digital signal is multiplied by a weighting factor.

13. The device of claim 1 wherein the neurological event detector device is further configured to process the at least one processed display channel and to detect neurological event activity based upon two or more detection algorithms that may be used concurrently to identify neurological event activity from a single processed display channel.

14. The device of claim 1 wherein said device is a workstation external to the patient's body.

15. The device of claim 1 wherein said at least one display device displays a first and a second processed display channel wherein said first processed display channel has at least one detection algorithm being chosen to detect the precursor of a seizure and said second processed display channel has at least one detection algorithm being chosen to detect ongoing in-seizure activity.

16. The device of claim 1 wherein said at least one display device displays electrical signal from the brain electrodes and the processed display channels.

17. The device of claim 1 further comprising an electrical stimulation therapy device implantable under the skin of a human body.

18. The device of claim 1 further comprising an electrical stimulation therapy device implantable under the scalp of a human body.

19. The device of claim 1 further comprising an electrical stimulation therapy device implantable into the cranium of a human body.

20. The device of claim 1 wherein the neurological event detector is configured to apply an amplitude duration detector algorithm to said at least one processed display channel for detecting an increase in signal amplitude in said at least one processed display channel for a specified time.

21. The device of claim 1 wherein the neurological event detector is configured to apply a DC shift algorithm to said at least one processed display channel for detecting a shift in the DC level of the processed display channel occurring over a specified time.

22. The device of claim 1 wherein the neurological event detector is configured to apply a zero crossing detector algorithm to said at least one processed display channel for detecting epileptiform activity when the number of zero crossings of said processed display channel is within a chosen range over a chosen length of time.

23. The device of claim 22 wherein the zero crossing detector algorithm also compares the average of the maximum and minimum amplitudes between the zero crossings with a chosen amplitude threshold.

24. The device of claim 1 wherein the neurological event detector is configured to apply a waveform detector algorithm to said at least one processed display channel for detecting when the number of half waves of a specified amplitude and minimum duration of said at least one processed display channel exceeds a preset limit over a chosen time.

25. The device of claim 24 wherein the settable parameter is the number of waves being exactly twice the number of half waves.

26. The device of claim 1 wherein the neurological event detector device is configured concurrently to apply two or more detection algorithms to different processed display channels to identify neurological event activity in each of said different processed display channels.

27. The device of claim 26 wherein the neurological event activity is epileptiform activity.

28. The device of claim 1 wherein the neurological event detector device is configured concurrently to apply two or more detection algorithms to different processed display channels to identify neurological event activity in two or more different processed display channels.

29. The device of claim 28 wherein the neurological event activity is epileptiform activity.

30. The device of claim 1 further comprising a seizure detection logic module configured to declare a valid seizure detection based on logical operations performed on the occurrence of a valid seizure detection in two or more processed display channels.

31. The device of claim 30 wherein said seizure detection logic module is configured to require that a seizure be detected in all processed display channels before declaring the seizure to be valid.

32. The device of claim 30 wherein said seizure detection logic module is configured to require that a seizure be detected in any processed display channel before declaring the seizure to be valid.

33. The device of claim 30 wherein seizure detection logic module is configured to require that a seizure be detected in a first processed display channel but not be detected in a second processed display channel before declaring the seizure to be valid.

34. The device of claim 1 wherein said detector algorithm is selected to reflect a neurological event in said patient.

35. The device of claim 1 wherein the detector algorithm is derived by detecting a neurological event in a specific human patient and forming said detector algorithm to detect that neurological event activity.

36. An implantable neuropacemaker assembly comprising:
   a multiplicity of intracranially placeable leads for delivering electrocortigram signals;
   at least one amplifier for amplifying the electrocortigram signals and produce amplified electrocortigram signals;
   at least one analog-to-digital converter for digitizing the amplified electrocortigram signals to produce a multiplicity of digital signals;
   at least one signal processor configured to produce one or more processed display channels, each processed display channel being a signal produced by the combination of one or more of the multiplicity of digital signals by signal processing with an algorithm having signal processing parameters; and
   at least one epileptiform event detector device configured to process said one or more processed display channel with programmable algorithms to detect epileptiform activity.

37. The implantable neuropacemaker assembly of claim 36 wherein said signal processor for the signal processing of said one or more of the digital signals to produce a processed display channel by low pass filtering.

38. The implantable neuropacemaker assembly of claim 36 wherein said signal processor for the signal processing of said one or more of the digital signals to produce a processed display channel by high pass filtering.

39. The implantable neuropacemaker assembly of claim 36 wherein said signal processor for the signal processing of said one or more of the digital signals to produce a processed display channel by bandpass filtering.

40. The implantable neuropacemaker assembly of claim 36 wherein said signal processor for the signal processing of said one or more of the digital signals to produce a processed display channel by the summing of two or more of the digital signals.

41. The implantable neuropacemaker assembly of claim 38 wherein in said summing of at least one of the digital signals with another, each digital signal is multiplied by a weighting factor.

42. The implantable neuropacemaker assembly of claim 36 wherein said signal processor for the signal processing of one or more of the digital signals to produce a processed display channel by the subtraction of at least one of the digital signals from another.

43. The implantable neuropacemaker assembly of claim 42 wherein in said subtraction of at least one of the digital signals from another, each digital signal is multiplied by a weighting factor.

44. The implantable neuropacemaker assembly of claim 36 wherein the epileptiform event detector device is further configured to process the at least one processed display channel and to detect epileptiform event activity based upon two or more detection algorithms that may be used concurrently to identify epileptiform event activity from a single processed display channel.

45. The implantable neuropacemaker assembly of claim 36 wherein said epileptiform event detector is configured to produce a first and a second processed display channel wherein said first processed display channel has at least one detection algorithm being chosen to detect the precursor of a seizure and said second processed display channel has at least one detection algorithm being chosen to detect ongoing in-seizure activity.

46. The implantable neuropacemaker assembly of claim 36 configured for implantation under the skin of a human body.

47. The implantable neuropacemaker assembly of claim 36 configured for implantation under the scalp of a human body.

48. The implantable neuropacemaker assembly of claim 37 configured for implantation into the cranium of a human body.

49. The implantable neuropacemaker assembly of claim 36 wherein the epileptiform event detector is configured to apply an amplitude duration detector algorithm to said at least one processed display channel for detecting an increase in signal amplitude in said at least one processed display channel for a specified time.

50. The implantable neuropacemaker assembly of claim 36 wherein the epileptiform event detector is configured to apply a DC shift algorithm to said at least one processed display channel for detecting a shift in the DC level of the processed display channel occurring over a specified time.

51. The implantable neuropacemaker assembly of claim 36 wherein the epileptiform event detector is configured to apply a zero crossing detector algorithm to said at least one processed display channel for detecting epileptiform activity when the number of zero crossings of said processed display channel is within a chosen range over a chosen length of time.

52. The implantable neuropacemaker assembly of claim 51 wherein the zero crossing detector algorithm also compares the average of the maximum and minimum amplitudes between the zero crossings with a chosen amplitude threshold.

53. The implantable neuropacemaker assembly of claim 36 wherein the epileptiform event detector is configured to apply a waveform detector algorithm to said at least one processed display channel for detecting when the number of half waves of a specified amplitude and minimum duration of said at least one processed display channel exceeds a preset limit over a chosen time.

54. The implantable neuropacemaker assembly of claim 53 wherein the settable parameter is the number of waves being exactly twice the number of half waves.

55. The implantable neuropacemaker assembly of claim 36 wherein the epileptiform event detector device is configured concurrently to apply two or more detection algorithms to different processed display channels to identify epileptiform event activity in each of said different processed display channels.

56. The implantable neuropacemaker assembly of claim 36 wherein the epileptiform event detector device is configured concurrently to apply two or more detection algorithms to different processed display channels to identify epileptiform event activity in two or more different processed display channels.

57. The implantable neuropacemaker assembly of claim 36 further comprising a seizure detection logic module configured to declare a valid seizure detection based on logical operations performed on the occurrence of a valid seizure detection in two or more processed display channels.

58. The implantable neuropacemaker assembly of claim 57 wherein said seizure detection logic module is configured to require that a seizure be detected in all processed display channels before declaring the seizure to be valid.

59. The implantable neuropacemaker assembly of claim 57 wherein said seizure detection logic module is configured to require that a seizure be detected in any processed display channel before declaring the seizure to be valid.

60. The implantable neuropacemaker assembly of claim 57 wherein seizure detection logic module is configured to require that a seizure be detected in a first processed display channel but not be detected in a second processed display channel before declaring the seizure to be valid.

61. The device of claim 36 wherein the detector algorithm is derived by detecting epileptiform activity in a specific human patient and forming said programmable algorithm to detect that epileptiform activity.

62. A device for detecting an epileptiform activity from a multiplicity of digitized EEG signals comprising:
at least one processed display channel processor configured to produce at least one processed display channel by signal processing of at least one of the multiplicity of digitized EEG signals, said signal processing having one or more parameters;
at least one epileptiform activity detector having at least one detector algorithm operating on the at least one processed display channel, the epileptiform activity detector having at least one programmable detection parameter, the epileptiform activity detector being configured to detect epileptiform activity based upon i.) the at least one processed display channel signal, ii.) the parameters of the signal processing used to create the at least one processed display channel, and iii.) said at least one detector algorithm having at least one detector parameter customizable for each patient.

63. The device of claim 62 wherein the at least one processed display channel processor for the signal processing of the at least one of the multiplicity of digitized EEG signals produces a processed display channel by low pass filtering.

64. The device of claim 62 wherein the at least one processed display channel processor for the signal processing of the at least one of the multiplicity of digitized EEG signals produces a processed display channel by high pass filtering.

65. The device of claim 62 wherein the at least one processed display channel processor for the signal processing of the at least one of the multiplicity of digitized EEG signals produces a processed display channel by bandpass filtering.

66. The device of claim 62 wherein the at least one processed display channel processor for the signal processing of the at least one of the multiplicity of digitized EEG signals produces a processed display channel by summing of two or more of the digitized EEG signals.

67. The device of claim 66 wherein in said summing of the at least one of the multiplicity of digitized EEG signals with each another, each digitized EEG signal is multiplied by a weighting factor.

68. The device of claim 62 wherein the at least one processed display channel processor for the signal processing of the at least one of the multiplicity of digitized EEG signals produces a processed display channel by the subtraction of at least one of the digitized EEG signals from another.

69. The device of claim 68 wherein in said subtraction of at least one of the digitized EEG signals from another, each digitized EEG signal is multiplied by a weighting factor.

70. The device of claim 62 wherein the epileptiform activity detector is further configured to process the at least one processed display channel and to detect epileptiform activity based upon two or more detection algorithms that may be used concurrently to identify epileptiform activity from a single processed display channel.

71. The device of claim 62 wherein said epileptiform activity detector is configured to produce a first and a second processed display channel wherein said first processed display channel has at least one detection algorithm being chosen to detect the precursor of a seizure and said second processed display channel has at least one detection algorithm being chosen to detect ongoing in-seizure activity.

72. The device of claim 62 wherein said device is a workstation external to the patient's body.

73. The device of claim 72 wherein the workstation is configured to display digitized EEG signals and processed display channels.

74. The device of claim 62 configured for implantation under the skin of a human body.

75. The device of claim 62 configured for implantation under the scalp of a human body.

76. The device of claim 62 configured for implantation into the cranium of a human body.

77. The device of claim 62 wherein the epileptiform activity detector is configured to apply an amplitude duration detector algorithm to said at least one processed display channel for detecting an increase in signal amplitude in said at least one processed display channel for a specified time.

78. The device of claim 62 wherein the epileptiform activity detector is configured to apply a DC shift algorithm to said at least one processed display channel for detecting a shift in the DC level of the processed display channel occurring over a specified time.

79. The device of claim 62 wherein the epileptiform activity detector is configured to apply a zero crossing detector algorithm to said at least one processed display channel for detecting epileptiform activity when the number of zero crossings of said processed display channel is within a chosen range over a chosen length of time.

80. The device of claim 79 wherein the zero crossing detector algorithm also compares the average of the maximum and minimum amplitudes between the zero crossings with a chosen amplitude threshold.

81. The device of claim 62 wherein the epileptiform activity detector is configured to apply a waveform detector algorithm to said at least one processed display channel for detecting when the number of half waves of a specified amplitude and minimum duration of said at least one processed display channel exceeds a preset limit over a chosen time.

82. The device of claim 81 wherein the settable parameter is the number of waves being exactly twice the number of half waves.

83. The device of claim 62 wherein the epileptiform activity detector device is configured concurrently to apply two or more detection algorithms to different processed display channels to identify epileptiform activity in each of said different processed display channels.

84. The device of claim 62 wherein the epileptiform activity detector device is configured concurrently to apply two or more detection algorithms to different processed display channels to identify epileptiform event activity in two or more different processed display channels.

85. The device of claim 62 further comprising a seizure detection logic module configured to declare a valid seizure detection based on logical operations performed on the occurrence of a valid seizure detection in two or more processed display channels.

86. The device of claim 85 wherein said seizure detection logic module is configured to require that a seizure be detected in all processed display channels before declaring the seizure to be valid.

87. The device of claim 85 wherein said seizure detection logic module is configured to require that a seizure be detected in any processed display channel before declaring the seizure to be valid.

88. The device of claim 85 wherein seizure detection logic module is configured to require that a seizure be detected in a first processed display channel but not be detected in a second processed display channel before declaring the seizure to be valid.

89. The device of claim 62 wherein said detector algorithm is selected to reflect a neurological event in said patient.

90. The device of claim 62 wherein the detector algorithm is derived by detecting epileptiform activity in a specific human patient and forming said detector algorithm to detect that epileptiform activity.

91. A device for diagnosis of, testing for, and treatment of epileptic seizures of a human patient, the device comprising:
- a multiplicity of brain electrodes configured to receive neural electrical signals generated by the brain of the human patient;
- conductors for carrying electrical signals to and from the multiplicity of brain electrodes;
- a physician's workstation configured to detect the presence of epileptiform activity by signal processing of at least one electrical signal received by the multiplicity of brain electrodes, the signal processing including analyzing a processed display channel using a processed display channel based seizure detector, the processed display channel based seizure detector having seizure detector parameters adjustable by a user best to detect epileptiform activity for a selected human patient;
- an implantable neuropacemaker configured to detect the presence of epileptiform activity by processing of at least one electrical signal received by the multiplicity of brain electrodes into at least one processed display channel and analysis of the at least one processed display channel for epileptiform activity using seizure detector having seizure detector parameters; and
- a transmitter configured to transmit to the neuropacemaker, the seizure detector parameters from the physician's workstation that have been selected to detect the epileptiform activity for the human patient.

92. The device of claim 91 further comprising a neural stimulator controller configured to initiate electrical stimulation to one or more of said brain electrodes upon detection of epileptiform activity.

93. A device for detection of epileptiform activity from a patient's brain comprising:
- at least one brain electrode, an amplifier, a digital to analog converter, and a processed display channel processor,
- wherein said at least one brain electrode is configured to electronically communicate signal information from a patient's brain to said amplifier, said amplifier being configured to amplify said signal information and produce amplified signals,
- wherein said analog to digital converter is configured to electronically receive said amplified signals from said amplifier and convert said amplified signals to digital signals,
- wherein said processed display channel processor is configured to process said multiple digital signals with an algorithm according to programmable algorithm rules to produce a processed display channel signal, said programmable algorithm rules being configured to produce a processed display channel signal clearly exhibiting characteristics of epileptiform activity within the patient's brain.

94. An implantable neuropacemaker comprising:
- at least one intracranially placed lead, an amplifier, an analog to digital converter, a signal processor, and an epileptiform activity detector module,
- said intracranially placed lead being configured to receive EEG signals from the brain of a patient and transmit said signals to said amplifier,
- said amplifier being configured to amplify said signals and produce amplified signals,
- said analog to digital converter being configured to electronically receive said amplified signals and convert said amplified signals to a multiplicity of digital signals,
- said signal processor being configured to process said multiple digital signals according to programmable parameters to produce a processed display channel signal exhibiting characteristics of epileptiform activity within the patient's brain,
- said epileptiform activity detector module being configured to detect epileptiform activity based upon processing of said processed display channel signal using a detection algorithm.

95. A device for detecting an epileptiform activity from a multiplicity of digitized EEG signals comprising:
- one or more brain electrodes configured to receive EEG signals from the brain of a patient;
- one or more processed display channel processors to produce processed display channels, each processed display channel comprising one or more EEG signals combined using digital signal processing;
- an epileptiform activity detector having detector algorithms operating on said one or more processed display channels, the epileptiform activity detector being configured to detect epileptiform activity,
- wherein the position of each brain electrode, the parameters of the signal processing used to create the processed display channel, and the algorithms used by the epileptiform activity detector being customized for each patient.

96. A device for diagnosis, testing, and treatment of epileptic seizures of a human patient, the device comprising:
   at least one intracranially placed lead, an amplifier, an analog to digital converter, a signal processor, and an epileptiform activity detection module,
   said intracranially placed lead being configured to receive EEG signals from the brain of a patient and transmit said signals to said amplifier,
   said amplifier being configured to amplify said signals and produce amplified signals,
   said analog to digital converter being configured to electronically receive said amplified signals and convert said amplified signals to a multiplicity of digital signals,
   said signal processor being configured to process said multiple digital signals according to programmable parameters to produce a processed display channel signal, said programmable parameters being configured to produce a processed display channel signal exhibiting characteristics of epileptiform activity within the patient's brain,
   said epileptiform activity detection module being configured to detect epileptiform activity based upon processing of said processed display channel signal;
   said amplifier, analog to digital converter, signal processor, and epileptiform activity detection algorithm comprising an implantable neuropacemaker module;
   said device further comprising a physician's workstation configured to transmit said programmable parameters to said implantable neuropacemaker module using a communication device.

97. A method for diagnosing and treating neurological disorders in a human patient comprising the steps of:
   signal processing digital signals related to a patient's EEG signals by combining said patient's EEG signals according to programmable parameters to produce processed display channel signals, the programmable parameters being selected to produce a processed display channel signal exhibiting characteristics of epileptiform activity within the patient's brain; and
   analyzing said processed display channel signal with an epileptiform activity detection algorithm configured to detect epileptiform activity based upon processing of said processed display channel signal.

98. The process of claim 97 additionally comprising the steps of:
   implanting at least one intracranially placed lead to a configuration wherein said lead receives EEG signals from the brain of the patient and transmits said signals to an amplifier; and
   amplifying said signals and transmitting them to an analog to digital converter to convert said signals into a multiplicity of said digital signals.

99. The process of claim 97 wherein said signal processing step comprises low pass filtering.

100. The process of claim 97 wherein said signal processing step comprises high pass filtering.

101. The process of claim 97 wherein said signal processing step comprises bandpass filtering.

102. The process of claim 97 wherein said signal processing step comprises summing of two or more of the digital signals.

103. The process of claim 102 wherein said signal in said summing of two or more of the digital signals, each digital signal is multiplied by a weighting factor.

104. The process of claim 97 wherein said signal processing step comprises subtraction of at least one of the digital signals from another.

105. The process of claim 97 wherein said signal processing step comprises subtraction of at least one of the digital signals from another, each digital signal is multiplied by a weighting factor.

106. The process of claim 97 wherein said analysis step comprises detecting neurological event activity based upon two or more detection algorithms used concurrently to identify neurological event activity from a single processed display channel.

107. The process of claim 97 further comprising displaying on a display device a first and a second processed display channel wherein said first processed display channel has an associated detection algorithm being chosen to detect the precursor of a seizure and said second processed display channel has an associated detection algorithm being chosen to detect ongoing in-seizure activity.

108. The process of claim 107 further comprising displaying on a display device electrical signals from the brain electrodes and the processed display channels.

109. The process of claim 97 wherein said analyzing step comprises applying an amplitude duration detector algorithm to said at least one processed display channel for detecting an increase in signal amplitude in said at least one processed display channel for a specified time.

110. The process of claim 97 wherein said analyzing step comprises applying a DC shift algorithm to said at least one processed display channel for detecting a shift in the DC level of the processed display channel occurring over a specified time.

111. The process of claim 97 wherein said analyzing step comprises applying a zero crossing detector algorithm to said at least one processed display channel for detecting epileptiform activity when the number of zero crossings of said processed display channel is within a chosen range over a chosen length of time.

112. The process of claim 111 wherein said zero crossing detector algorithm also compares the average of the maximum and minimum amplitudes between the zero crossings with a chosen amplitude threshold.

113. The process of claim 97 wherein said analyzing step comprises applying a waveform detector algorithm to said at least one processed display channel for detecting when the number of half waves of a specified amplitude and minimum duration of said at least one processed display channel exceeds a preset limit over a chosen time.

114. The process of claim 97 wherein said analyzing step comprises concurrently applying two or more detection algorithms to different processed display channels to identify neurological event activity in each of said different processed display channels.

115. The process of claim 97 wherein said analyzing step comprises concurrently applying two or more detection algorithms to different processed display channels to identify neurological event activity in two or more different processed display channels.

116. The process of claim 97 wherein said analyzing step further comprises declaring a valid seizure detection based on logical operations performed on the occurrence of a valid seizure detection in two or more processed display channels.

117. The process of claim 97 wherein said analyzing step further comprises declaring a valid seizure detection based on logical operations performed on the occurrence of a valid seizure detection in all processed display channels.

118. The process of claim 97 wherein said analyzing step further comprises declaring a valid seizure detection based on logical operations performed on the occurrence of a valid seizure detection in any processed display channels.

119. The process of claim 97 wherein said analyzing step further comprises declaring a valid seizure detection based on the occurrence of a valid seizure detection in a first processed display channel but not detected in a second processed display channel.

* * * * *